(12) United States Patent
Simon et al.

(10) Patent No.: US 11,926,631 B2
(45) Date of Patent: Mar. 12, 2024

(54) METHOD OF TREATING CANCER USING AMANITIN DERIVATIVES

(71) Applicant: Heidelberg Pharma Research GmbH, Ladenburg (DE)

(72) Inventors: Werner Simon, Ladenburg (DE); Susanne Werner-Simon, Ladenburg (DE); Christian Lutz, Ladenburg (DE); Christoph Müller, Ladenburg (DE); Torsten Hechler, Ladenburg (DE); Michael Kulke, Ladenburg (DE)

(73) Assignee: Heidelberg Pharma Research GmbH, Ladenburg (DE)

( * ) Notice: Subject to any disclaimer, the term of this patent is extended or adjusted under 35 U.S.C. 154(b) by 0 days.

(21) Appl. No.: 17/742,196

(22) Filed: May 11, 2022

(65) Prior Publication Data
US 2022/0274995 A1    Sep. 1, 2022

Related U.S. Application Data

(62) Division of application No. 16/637,361, filed as application No. PCT/EP2018/071265 on Aug. 6, 2018, now Pat. No. 11,420,971.

(30) Foreign Application Priority Data

Aug. 7, 2017 (EP) ..................................... 17185181

(51) Int. Cl.
| | | |
|---|---|---|
| *A61P 35/00* | (2006.01) | |
| *A61K 47/68* | (2017.01) | |
| *C07D 487/04* | (2006.01) | |
| *C07K 1/06* | (2006.01) | |
| *C07K 7/64* | (2006.01) | |

(52) U.S. Cl.
CPC ........ *C07D 487/04* (2013.01); *A61K 47/6831* (2017.08); *A61P 35/00* (2018.01); *C07K 1/063* (2013.01); *C07K 7/64* (2013.01)

(58) Field of Classification Search
None
See application file for complete search history.

(56) References Cited

U.S. PATENT DOCUMENTS

| | | | |
|---|---|---|---|
| 5,939,598 | A | 8/1999 | Kucherlapati et al. |
| 9,233,173 | B2 * | 1/2016 | Faulstich ............ A61K 47/6855 |
| 9,295,729 | B2 | 3/2016 | Smith et al. |
| 11,420,971 | B2 | 8/2022 | Simon et al. |
| 2016/0220687 | A1 | 8/2016 | Alhamdan |
| 2020/0181200 | A1 | 6/2020 | Lutz et al. |
| 2021/0061805 | A1 | 3/2021 | Simon et al. |

FOREIGN PATENT DOCUMENTS

| | | |
|---|---|---|
| EP | 2497499 A1 | 9/2012 |
| WO | WO 2010/115629 A2 | 10/2010 |
| WO | WO 2010/115630 A1 | 10/2010 |
| WO | WO 2012/041504 A1 | 4/2012 |
| WO | WO 2012/119787 A1 | 9/2012 |
| WO | WO 2014/009025 A1 | 1/2014 |
| WO | WO 2014/043403 A1 | 3/2014 |
| WO | WO 2016/059622 A2 | 4/2016 |
| WO | WO 2017/046658 A1 | 3/2017 |
| WO | WO 2017/089607 A1 | 6/2017 |
| WO | WO 2019/030173 A1 | 2/2019 |

OTHER PUBLICATIONS

Kume, K. et al. α-Amanitin Restrains Cancer Relapse from Drug-Tolerant Cell Subpopulations via TAF15. Sci. Rep. 6, 25895; (2016) (Year: 2016).*

Agarwal et al., "Hydrazino-Pictet-Spengler Ligation as a Biocompatible Method for the Generation of Stable Protein Conjugates," *Bioconjugate Chemistry*, 24(6): 846-851 (2013).

Badescu et al., "Bridging Disulfides for Stable and Defined Antibody Drug Conjugates," *Bioconjugate Chemistry*, 25(6): 1124-1136 (2014).

Bryden et al., "Regioselective and Stoichiometrically Controlled Conjugation of Photodynamic Sensitizers to a HER2 Targeting Antibody Fragment," *Bioconjugate Chemistry*, 25(3): 611-617 (2014).

Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," *Bioconjugate Chemistry*, 13(4): 855-869 (2002).

Falck-Pedersen et al., "Regiospecific arylazo substitution into α-amanitin with retention of inhibitory properties against eukaryotic Class II RNA polymerase," *Int'l J. Peptide Protein Res.*, 21(4): 431-439 (1983).

Hu et al., "Stereocontrolled and Efficient Total Synthesis of (−)-Stephanotic Acid Methyl Ester and (−)-Celogentin C," *Organic Letters*, 12(5): 956-959 (2010).

Kolodych et al., "CBTF: New Amine-to-Thiol Coupling Reagent for Preparation of Antibody Conjugates with Increased Plasma Stability," *Bioconjugate Chemistry*, 26(2): 197-200 (2015).

Schumacher et al., "Next generation maleimides enable the controlled assembly of antibody-drug conjugates via native disulfide bond bridging," *Organic & Biomolecular Chemistry*, 12(37): 7261-7269 (2014).

Shen et al., "Disulfide Spacer between Methotrexate and Poly (D-lysine): A Probe for Exploring the Reductive Process in Endocytosis," *J. Biological Chemistry*, 260(20): 10905-10908 (1985).

(Continued)

*Primary Examiner* — Thomas S Heard

(74) *Attorney, Agent, or Firm* — Leydig, Voit & Mayer, Ltd.

(57) ABSTRACT

The invention relates to methods for synthesizing amanitin derivatives having an amino group attached to position 6' of the central tryptophan moiety. The invention furthermore relates to an amanitin derivative having an amino group attached to position 6' of the central tryptophan moiety, conjugates of such amanitin derivative, and pharmaceutical compositions comprising such conjugates.

4 Claims, 8 Drawing Sheets

(56) References Cited

OTHER PUBLICATIONS

Toda et al., "Rapid, Stable, Chemoselective Labeling of Thiols with Julia-Kocieński-like Reagents: A Serum-Stable Alternative to Maleimide-Based Protein Conjugation," *Angewandte Chemie International Edition*, 52(48): 12592-12596 (Nov. 25, 2013).

Wieland et al., "Amatoxins, Phallotoxins, Phallolysin, and Antamanide: The Biologically Active Components of Poisonous Amanita Mushrooms," *CRC Critical Reviews in Biochemistry*, 5(3): 185-260 (1978).

Nakagawa et al., "Dye-Sensitized Photo-Oxygenation of Tryptophan," *Tetrahedron*, 41(11): 2125-2132 (1985).

Zanotti et al., "Structure-toxicity relationships in the amatoxin series: Synthesis of S-deoxy [γ(R)-hydroxy-Ile³]-amaninamide, its crystal and molecular structure and inhibitory efficiency," *Int'l J. of Peptide and Protein Research*, 34(3): 222-228 (1989).

European Patent Office, International Search Report in International Patent Application No. PCT/EP2018/071265. (dated Nov. 22, 2018).

European Patent Office, Written Opinion in International Patent Application No. PCT/EP2018/071265 (dated Nov. 22, 2018).

European Patent Office, Communication Pursuant to Article 94(3) EPC in European Patent Application No. 18746964.8 (dated May 30, 2022).

U.S. Appl. No. 16/637,361, filed Feb. 7, 2020.

Bensaude, "Inhibiting Eukaryotic Transcription," *Transcription*, 2(3): 103-108 (2011).

Laham-Karam et al., "Transcription and Translation Inhibitors in Cancer Treatment," *Frontiers in Chemistry*, 8: 276 (2020).

Wieland et al., "Fifty Years of Amanitin," *Experientia*, 47: 1186-1193 (1991).

European Aptent Office, Communication Pursuant to Article 94(3) EPC in European Patent Application No. 18746964.8 (dated Mar. 30, 2023).

Japan Patent Office, Notice of Rejection in Japanese Patent Application No. 2020-506728 (dated Jun. 7, 2022).

Japan Patent Office, Notice of Rejection in Japanese Patent Application No. 2020-506728 (dated Sep. 27, 2022).

\* cited by examiner

|               | R₁  | R₂  | R₃   | R₄  |
|---------------|-----|-----|------|-----|
| α-amanitin    | OH  | OH  | NH₂  | OH  |
| β-amanitin    | OH  | OH  | OH   | OH  |
| γ-amanitin    | H   | OH  | NH₂  | OH  |
| ε-amanitin    | H   | OH  | OH   | OH  |
| amanin        | OH  | OH  | OH   | H   |
| amaninamide   | OH  | OH  | NH₂  | H   |
| amanullin     | H   | H   | NH₂  | OH  |
| amanullinic acid | H | H  | OH   | OH  |
| γ-amanin      | H   | OH  | OH   | H   |
| γ-amaninamide | H   | OH  | NH2  | H   |

HDP 30.2528

HDP 30.2524

HDP 30.2540

HDP 30.1699

METHOD OF TREATING CANCER USING AMANITIN DERIVATIVES

CROSS-REFERENCE TO RELATED APPLICATIONS

This patent application is a divisional of copending U.S. patent application Ser. No. 16/637,361, filed on Feb. 7, 2020, which is the U.S. national phase of International Patent Application No. PCT/EP2018/071265, filed on Aug. 6, 2018, which claims the benefit of European Patent Application No. 17185181.9, filed on Aug. 7, 2017, the disclosures of which are incorporated herein by reference in their entireties for all purposes.

FIELD OF THE INVENTION

The invention relates to methods for synthesizing amanitin derivatives having an amino group attached to position 6' of the central tryptophan moiety. The invention furthermore relates to an amanitin derivative having an amino group attached to position 6' of the central tryptophan moiety, conjugates of such amanitin derivative, and pharmaceutical compositions comprising such conjugates.

BACKGROUND OF THE INVENTION

Amatoxins are cyclic peptides composed of 8 amino acids that are found in *Amanita phalloides* mushrooms (see FIG. 1). Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA-polymerase II is very tight ($K_D$=3 nM). Dissociation of amanitin from the enzyme is a very slow process, thus making recovery of an affected cell unlikely. When the inhibition of transcription lasts too long, the cell will undergo programmed cell death (apoptosis).

The use of amatoxins as cytotoxic moieties for tumour therapy had already been explored in 1981 by coupling an anti-Thy 1.2 antibody to α-amanitin using a linker attached to the indole ring of Trp (amino acid 4; see FIG. 1) via diazotation (Davis & Preston, Science 213 (1981) 1385-1388). Davis & Preston identified the site of attachment as position 7'. Morris & Venton demonstrated as well that substitution at position 7' results in a derivative, which maintains cytotoxic activity (Morris & Venton, Int. J. Peptide Protein Res. 21 (1983) 419-430).

Patent application EP 1 859 811 A1 (published Nov. 28, 2007) described conjugates, in which the γ C-atom of amatoxin amino acid 1 of β-amanitin was directly coupled, i.e. without a linker structure, to albumin or to monoclonal antibody HEA125, OKT3, or PA-1. Furthermore, the inhibitory effect of these conjugates on the proliferation of breast cancer cells (MCF-7), Burkitt's lymphoma cells (Raji) and T-lymphoma cells (Jurkat) was shown. The use of linkers was suggested, including linkers comprising elements such as amide, ester, ether, thioether, disulfide, urea, thiourea, hydrocarbon moieties and the like, but no such constructs were actually shown, and no more details, such as attachment sites on the amatoxins, were provided.

Patent applications WO 2010/115629 and WO 2010/115630 (both published Oct. 14, 2010) describe conjugates, where antibodies, such as anti-EpCAM antibodies such as humanized antibody huHEA125, are coupled to amatoxins via (i) the γ C-atom of amatoxin amino acid 1, (ii) the 6' C-atom of amatoxin amino acid 4, or (iii) via the δ C-atom of amatoxin amino acid 3, in each case either directly or via a linker between the antibody and the amatoxins. The suggested linkers comprise elements such as amide, ester, ether, thioether, disulfide, urea, thiourea, hydrocarbon moieties and the like. Furthermore, the inhibitory effects of these conjugates on the proliferation of breast cancer cells (cell line MCF-7), pancreatic carcinoma (cell line Capan-1), colon cancer (cell line Colo205), and cholangiocarcinoma (cell line OZ) were shown.

Patent application WO 2012/119787 describes that target-binding moieties can be attached to amatoxins via linkers at additional attachment sites on tryptophan amino acid 4, namely positions 1'-N, without interference with the interaction of such amatoxins with their target, the DNA-dependent RNA polymerase II of mammalian cells.

Patent application WO 2014/009025 describes the total synthesis of amanitin derivatives using a synthon for γ,δ-dihydroxyisoleucine as one of the starting materials. Furthermore, patent application PCT/EP2016/078984 [published as WO 2017/089607] describes the total synthesis of derivatives of δ- and ε-amanitin using readily available (2S,3R,4S)-L-4-hydroxyisoleucine as one of the starting materials. However, these approaches, and all other fully or partially synthetic approaches pursued so far, are incorporating the central tryptophan moiety into the amatoxin core by using the method according to Savige-Fontana. In this method, cis-2-carboxy-3a-hydroxy-1,2,3,3a,8,8a-hexahydropyrrolo[2,3-b]indole ("Hpi") is incorporated into a linear amanitin precursor structure. In an acid-catalyzed Hpi-cysteine coupling reaction, the amanitin ring system with central tryptophan moiety is formed.

Hpi, however, does not possess any functional moiety attached to the phenyl ring of Hpi's indole moiety. Thus, the amanitin products resulting from the method according to Savige-Fontana contain a central tryptophan moiety without any further substituents. Naturally occurring α-, γ, and ε-amanitins, however, contain a central 6'-hydoxy-tryptophan moiety, and that 6'-hydroxy group has successfully been used as functional group for the functionalization of amanitins, e.g. by attaching targeting moieties, either directly or via linkers (see, for example, WO 2010/115629, WO 2010/115630, and WO/2012/041504). Thus, in the case of synthetic amanitins, functionalization had to be done via (i) the γ C-atom of amatoxin amino acid 1, or (ii) via the δ C-atom of amatoxin amino acid 3, as described above, or via the nitrogen atom of the tryptophan moiety, as described in WO 2012/119787.

Hpi can be obtained by reacting tryptophan with peracetic acid or photochemically with singlet oxygen. However, no derivatives with substituents attached to the phenyl ring of Hpi's indole moiety have been described so far.

While the use of fully synthetic routes to amatoxins may offer an option for the supply of larger quantities of amatoxins required for therapeutic uses, and may offer the construction of a variety of amatoxin variants by using appropriate starting materials as building blocks, the approaches pursued in the past had been limited by the fact that the native structure α-, β-, γ, and/or ε-amanitin could not yet be obtained, since the 6'-hydroxy moiety attached to the core tryptophan moiety in these amanitins could not be incorporated. Thus, options for functionalizing synthetic amanitins have been rather limited so far. Furthermore, reactivity of the phenolic hydroxy group is anyway not optimal so that alternative functional groups, such as amino groups would be particularly interesting, since it is highly desirous to expand the range of options available for the functionalization, since factors such as steric hindrance and reactivity might have a strong impact on the reactivity, biological activity and/or stability of synthetic amanitins and of conjugates thereof. However, stability and efficacy of conjugates comprising highly toxic amanitins are of utmost importance for the envisaged use as therapeutic molecules for administration to human beings.

So far, the introduction of amino functionalities in the tryptophan moiety has only been achieved by modification of full amatoxin moieties, e.g. by diazotation (Falck-Pedersen et al., Int. J. Peptide Protein Res. 21, 1983, 431-439) or nitration (WO 2017/046658). In the case of WO 2017/046658. however, the nitration reaction resulted in amatoxin derivatives that were nitrated in the 5'-position of the central tryptophan moiety. Thus, no approach has been described so far that permitted the introduction of an amino group in the 6'-position.

OBJECT OF THE INVENTION

Thus, there was still a great need for a cost efficient and robust way of synthesizing amatoxins with an amino group attached to the phenyl ring of the central tryptophan moiety, in particular in the 6'-position of the tryptophan moiety. In particular, there is a strong need for identifying starting materials that could be used in the established Savige-Fontana reaction and that are set up in a way that they can cause the incorporation of such amino groups.

SUMMARY OF THE INVENTION

The present invention is based on the unexpected observation that variants of Hpi can be synthesized that permit the introduction of an amino group during the synthesis of amanitin derivatives.

Thus, in one aspect the present invention relates to an amino-substituted derivative of 2-carboxy-3α-hydroxy-1,2,3,3a,8,8a-hexahydropyrrolo[2,3-b]indole according to Formula I

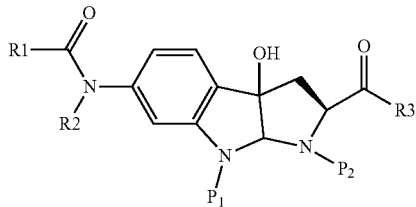

wherein R1 is selected from alkyl, aryl, heteroaryl, substituted alkyl, substituted aryl, and substituted heteroaryl; particularly wherein R1 is $CF_3$;
$P_1$, $P_2$ are each hydrogen or a protecting group, particularly a protecting group independently selected from Boc, PhCH$_2$OCO—, CH$_2$=CHCH$_2$O—CO—, and trityl;
R2 is selected from H, alkyl, aryl, substituted alkyl, and substituted aryl;
R3 is selected from OH, OR1, and a polypeptide chain consisting of 1-7 amino acid residues.

In a second aspect, the present invention relates to a method for the synthesis of a linear precursor comprising eight amino acid residues of an amanitin derivative comprising a 6'-amino-substituted tryptophan moiety, comprising the step of using an amino-substituted derivative of 2-carboxy-3α-hydroxy-1,2,3,3a,8,8a-hexahydropyrrolo[2,3-b]indole of the present invention in the peptide synthesis of said precursor.

In a third aspect, the invention relates to a method for the synthesis of an amanitin derivative comprising a 6'-amino-substituted tryptophan moiety, comprising the steps of.
(i) causing or allowing the formation of a bond between the cysteine residue and the tryptophan moiety of the linear precursor of the present invention; and
(ii) causing or allowing the formation of said amanitin derivative by reacting the N-terminus of the linear precursor the present invention with the C-terminus of said precursor.

In a fourth aspect, the invention relates to an amanitin derivative comprising a 6'-amino-substituted tryptophan moiety, which is selected from (i) S-desoxy-6'-amino-amanin, 6'-amino-amanin, (ii) S-desoxy-6'-amino-amaninamide, 6'-amino-amaninamide, (iii) a derivative of the amanitin derivative according to (i), wherein the free carboxylic acid moiety of amino acid 1 is converted to an carboxylic ester —C(=O)OR4 or to a moiety —C(=O)NH—OR4.

In a fifth aspect, the invention relates to a conjugate comprising (a) amanitin derivative comprising a 6'-amino-substituted tryptophan moiety of the present invention; (b) a target-binding moiety; and (c) optionally a linker linking said amanitin derivative and said target-binding moiety.

In a sixth aspect, the invention relates to a pharmaceutical composition comprising the amanitin of the present invention or the conjugate of the present invention.

In a seventh aspect, the invention relates to an amanitin derivative of the present invention, the conjugate of the present invention, or the pharmaceutical composition of the present invention for use in the treatment of cancer in a patient, particularly wherein the cancer is selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, leukemia, and malignant lymphoma.

In an eighth aspect, the invention relates to a construct comprising (a) an amanitin derivative of the present invention; and (b) a linker moiety carrying a reactive group Y for linking said amanitin derivative to a target-binding moiety.

Figure 7:
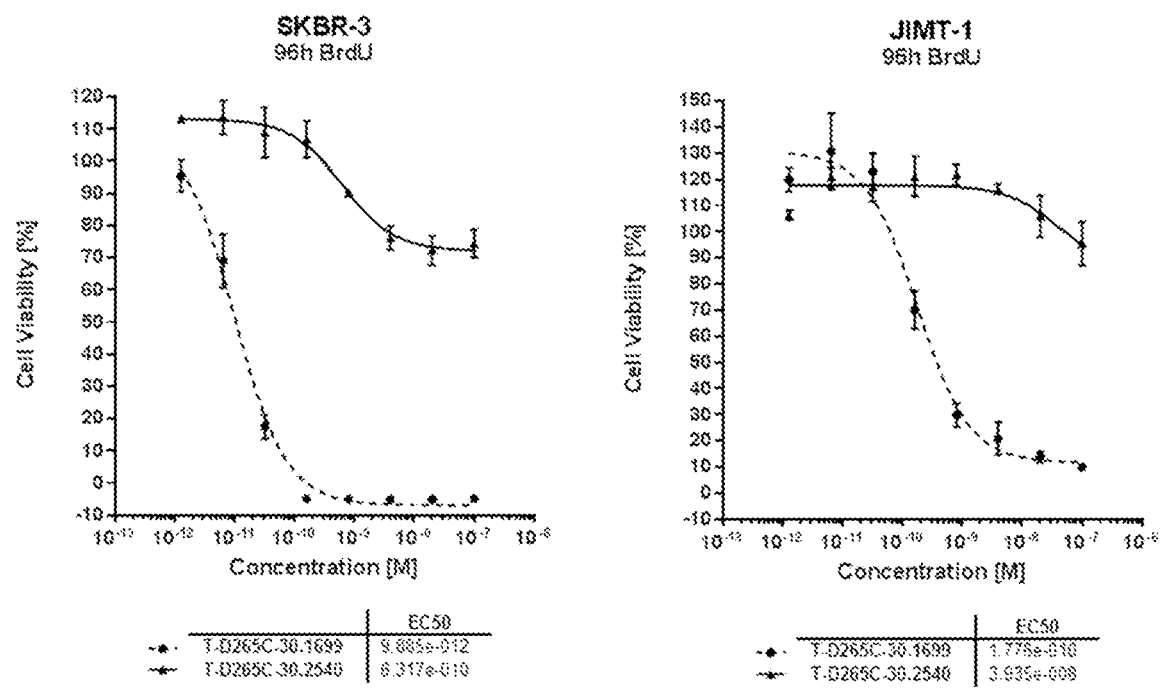

FIG. 7 shows the cytotoxicity of T-D265C-30.2540 targeting HER-2/neu on SKBR-3 cells (HER-2/neu+++) and JIMT-1 cells (HER-2/neu+) in comparison to T-D265C-30.1699

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Particularly, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer, composition or step or group of integers or steps, while any additional integer, composition or step or group of integers, compositions or steps may optionally be present as well, including embodiments, where no additional integer, composition or step or group of integers, compositions or steps are present. In such latter embodiments, the term "comprising" is used coterminous with "consisting of".

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety to the extent possible under the respective patent law. Nothing herein is to be construed as an admission that the invention is not entitled to antedate such disclosure by virtue of prior invention.

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The present invention is based on the unexpected observation that variants of Hpi can be synthesized that permit the introduction of amino groups during the synthesis of amanitin derivatives Thus, in one aspect the present invention relates to an amino-substituted derivative of 2-carboxy-3α-hydroxy-1,2,3,3a,8,8a-hexahydropyrrolo[2,3-b]indole according to Formula I

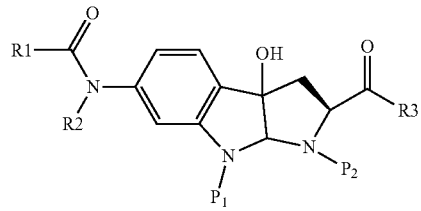

wherein R1 is selected from alkyl, aryl, heteroaryl, substituted alkyl, substituted aryl, and substituted heteroaryl; particularly wherein R1 is $CF_3$;

$P_1$, $P_2$ are each hydrogen or a protecting group;

R2 is selected from H, alkyl, aryl, substituted alkyl, and substituted aryl;

R3 is selected from OH, OR1, and a polypeptide chain consisting of 1-7 amino acid residues.

In the context of the present invention, the term "protecting group" refers to a group that is attached to a nitrogen atom in positions 1 or 8 of the central hexahydropyrrolo[2,3-b]indole moiety in order to block the nitrogen atom from reacting with other reactants used to synthesize and/or to further functionalize compounds according to Formula I. One of ordinary skill in the art is well familiar with the different protecting groups that are available in the art and that can be attached to the corresponding nitrogen atom when needed to protect the nitrogen atom, and that can be cleaved off subsequently, when N-protection is no longer needed. In particular embodiments, the N-protection uses an N-acylating reagent. Thus, in such embodiments, $P_1$ and/or $P_2$ are acyl groups. In particular other embodiments, the N-protection uses an N-alkylating reagent. Thus, in such embodiments, $P_1$ and/or $P_2$ is an alkyl group.

In particular embodiments, the protecting group $P_1$ or $P_2$, when present, is independently selected from Boc, $PhCH_2OCO$—, $CH_2$=$CHCH_2O$—CO—, and trityl.

In a particular embodiment, the hydroxy group in position 3a and the hydrogen atom in position 8a are in cis-configuration with respect to the functional group attached to position 2. In another particular embodiment, the hydroxy group in position 3a and the hydrogen atom in position 8a are in trans-configuration with respect to the functional group attached to position 2. In a particular embodiment, the amino-substituted derivative according to the present invention is a mixture of compounds with cis- and trans-configuration.

In a second aspect, the present invention relates to a method for the synthesis of a linear precursor comprising eight amino acid residues of an amanitin derivative comprising a 6'-amino-substituted tryptophan moiety, comprising the step of using an amino-substituted derivative of 2-carboxy-3α-hydroxy-1,2,3,3a,8,8a-hexahydropyrrolo[2,3-b]indole of the present invention in the peptide synthesis of said precursor.

In a third aspect, the invention relates to a method for the synthesis of an amanitin derivative comprising a 6'-amino-substituted tryptophan moiety, comprising the steps of.

(i) causing or allowing the formation of a bond between the cysteine residue and the tryptophan moiety of the linear precursor of the present invention; and (ii) causing or allowing the formation of said amanitin derivative by reacting the N-terminus of the linear precursor the present invention with the C-terminus of said precursor.

In additional aspects, the invention relates to individual amanitin precursors synthesized as shown in the examples, in particular compounds HDP 30.2516, HDP 30.2528 and the solid phase based intermediates synthesized according to [00137].

In a particular embodiment, the method of the present invention further comprises the oxidation of the sulfur atom of the cysteine moiety to form a sulfoxide or a sulfone, particularly a sulfoxide.

In a fourth aspect, the invention relates to an amanitin derivative comprising a 6'-amino-substituted tryptophan moiety, which is selected from (i) S-desoxy-6'-amino-amanin, 6'-amino-amanin, (ii) S-desoxy-6'-amino-amaninamide, 6'-amino-amaninamide, (iii) a derivative of the amanitin derivative according to (i), wherein the free carboxylic acid moiety of amino acid 1 is converted to an carboxylic ester —C(═O)OR4 or to a moiety —C(═O)NH—OR4.

In a particular embodiment, the amanitin derivative of the present invention is selected from S-desoxy-6'-amino-amanin, 6'-amino-amanin, S-desoxy-6'-amino-amaninamide, and 6'-amino-amaninamide.

In a fifth aspect, the invention relates to a conjugate comprising (a) an amanitin derivative comprising a 6'-amino-substituted tryptophan moiety of the present invention; (b) a target-binding moiety; and (c) optionally a linker linking said amanitin derivative and said target-binding moiety.

In a sixth aspect, the invention relates to a pharmaceutical composition comprising the amanitin of the present invention or the conjugate of the present invention.

In a seventh aspect, the invention relates to an amanitin derivative of the present invention, the conjugate of the present invention, or the pharmaceutical composition of the present invention for use in the treatment of cancer in a patient, particularly wherein the cancer is selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, leukemia, and malignant lymphoma.

In an eighth aspect, the invention relates to a construct comprising (a) an amanitin derivative of the present invention; and (b) a linker moiety carrying a reactive group Y for linking said amanitin derivative to a target-binding moiety.

In the context of the present invention, the term "amanitin" refers to a particular group of amatoxins. In the context of the present invention the term "amatoxin" includes all cyclic peptides composed of 8 amino acids as isolated from the genus *Amanita* and described in Wieland, T. and Faulstich H. (Wieland T, Faulstich H., CRC Crit Rev Biochem. 5 (1978) 185-260). In the context of the present invention, the term "amanitins" refers to bicyclic structure that are based on an aspartic acid or asparagine residue in position 1, a proline residue, particularly a hydroxyproline residue in position 2, an isoleucine, hydroxyisoleucine or dihydroxyisoleucine in position 3, a tryptophan or hydroxytryptophan residue in position 4, glycine residues in positions 5 and 7, an isoleucine residue in position 6, and a cysteine residue in position 8, particularly a derivative of cysteine that is oxidized to a sulfoxide or sulfone derivative (for the numbering and representative examples of amanitins, see FIG. 1), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in each case wherein any such derivative or analogue is functionally active by inhibiting mammalian RNA polymerase II. In the context of the present invention, the tryptophan residue in position 4 is replaced by a 6'-aminosubstituted derivative.

Thus, in the context of the present invention, the term "eight amino acid residues of an amanitin derivative" refers to the specific amino acids that form the bicyclic amanitin polypeptide structure.

Figure 1:
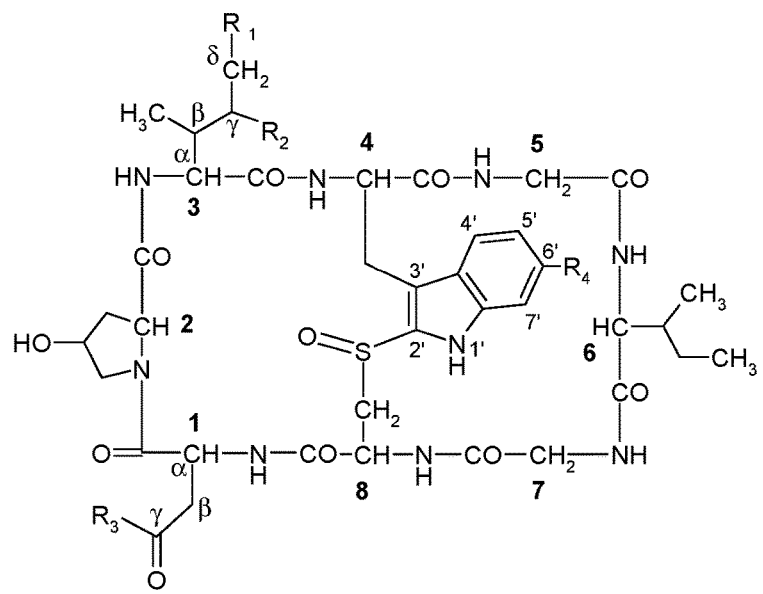
FIG. 1 shows the structural formulae of different amatoxins. The numbers in bold type (1 to 8) designate the standard numbering of the eight amino acids forming the amatoxin. The standard designations of the atoms in amino acids 1, 3 and 4 are also shown (Greek letters α to γ, Greek letters α to δ, and numbers from 1' to 7', respectively).
Figure 2:
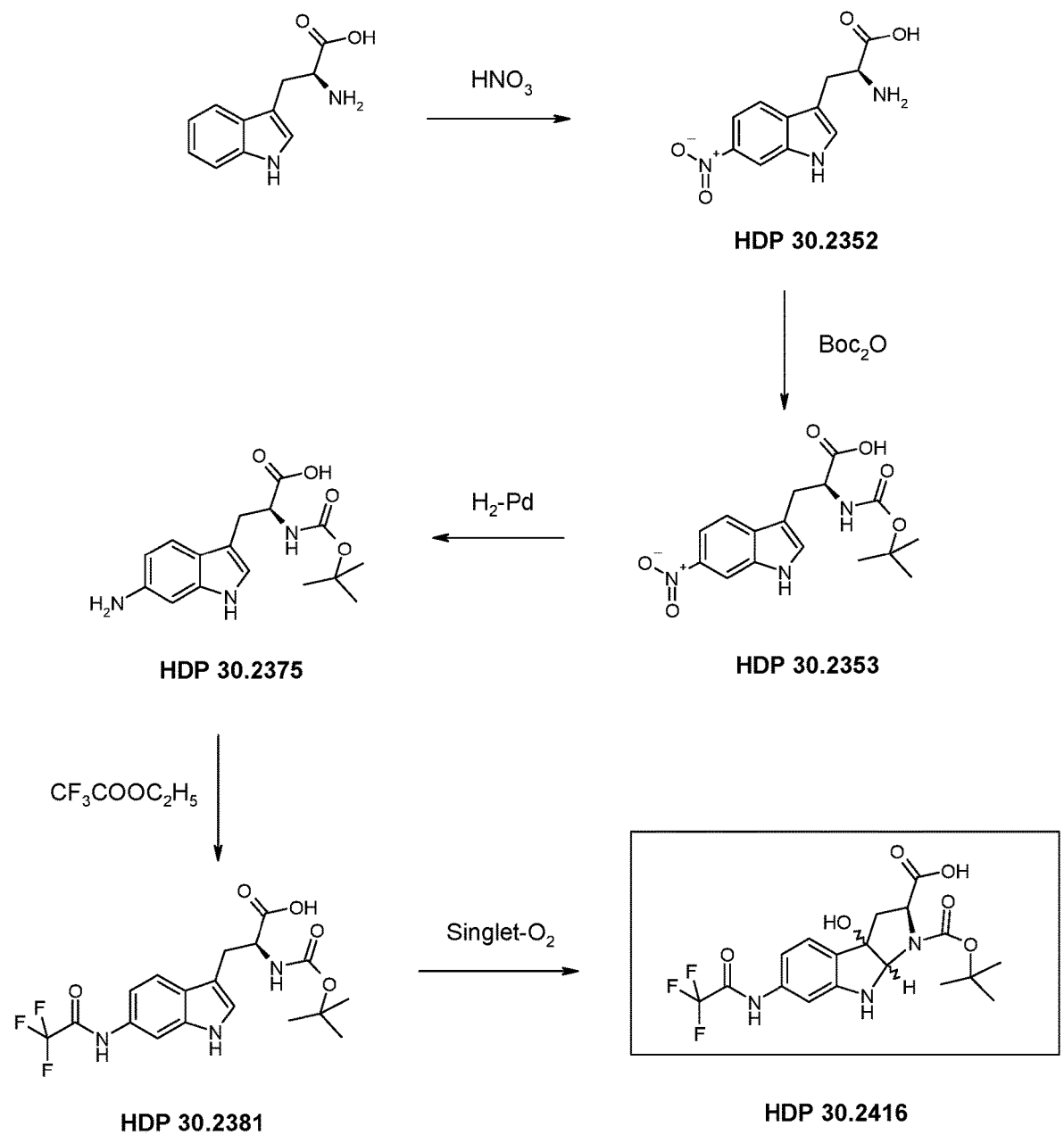
FIG. 2 shows the synthesis scheme for amino-substituted Hpi derivative HDP 30.2416.
Figure 3:
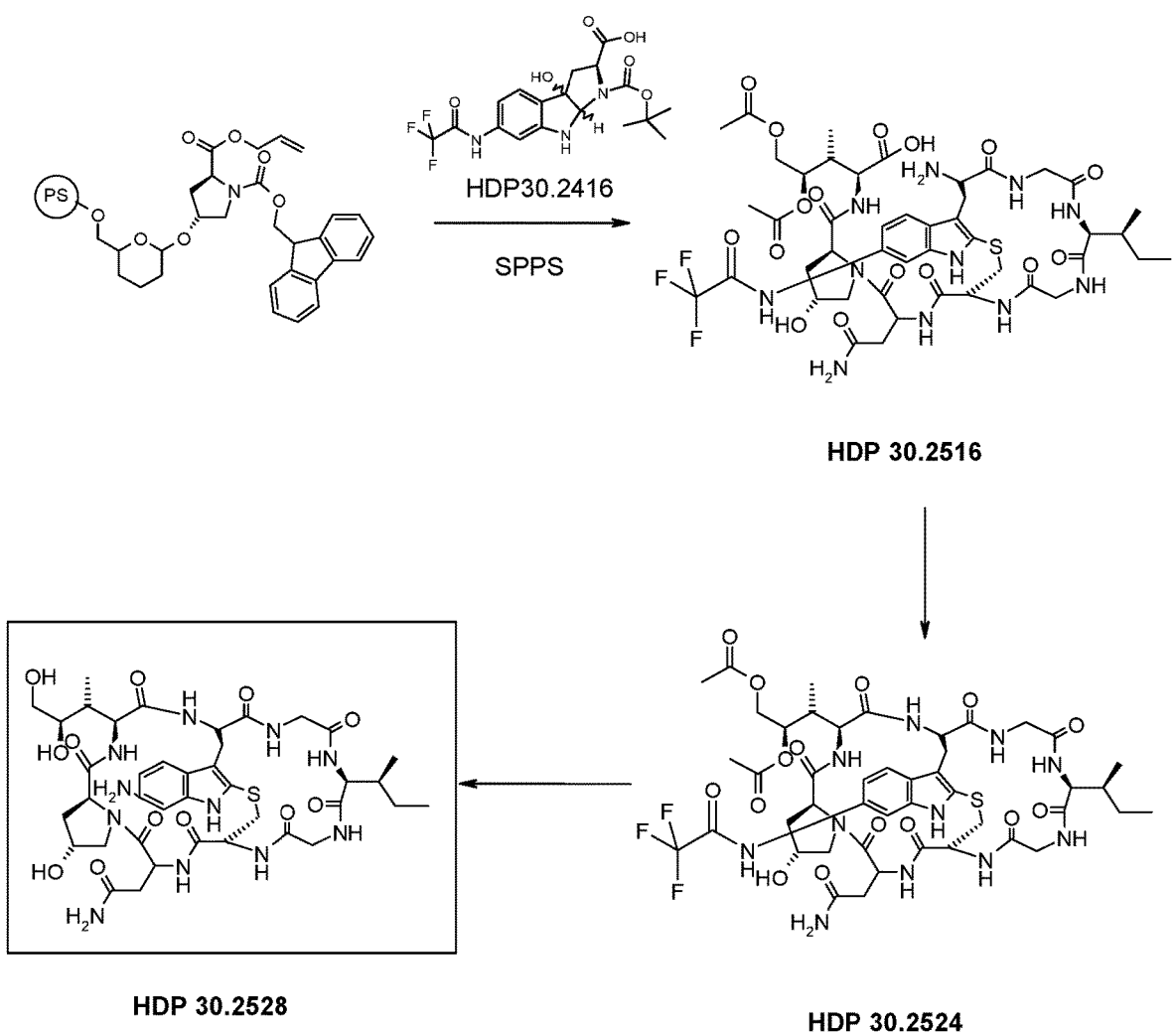
FIG. 3 shows the synthesis scheme for 6'.amino-amaninamide (HDP 30.2528).
Figure 4:
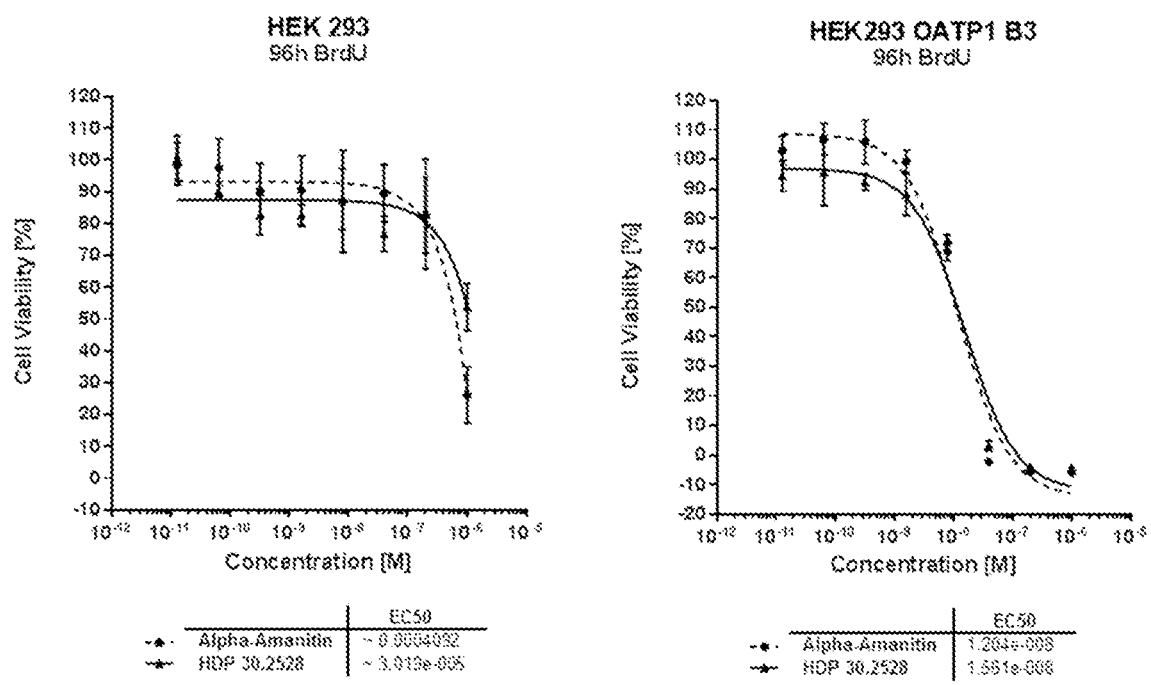
FIG. 4 shows the cytotoxicity of 6'.amino-amaninamide (HDP 30.2528) on HEK293 cells (EC$_{50}$=3.0 10$^{-6}$ M) and on HEK293 OATP1B3 cells (EC$_{50}$=3.0 10$^{-8}$ M).
Figure 5:
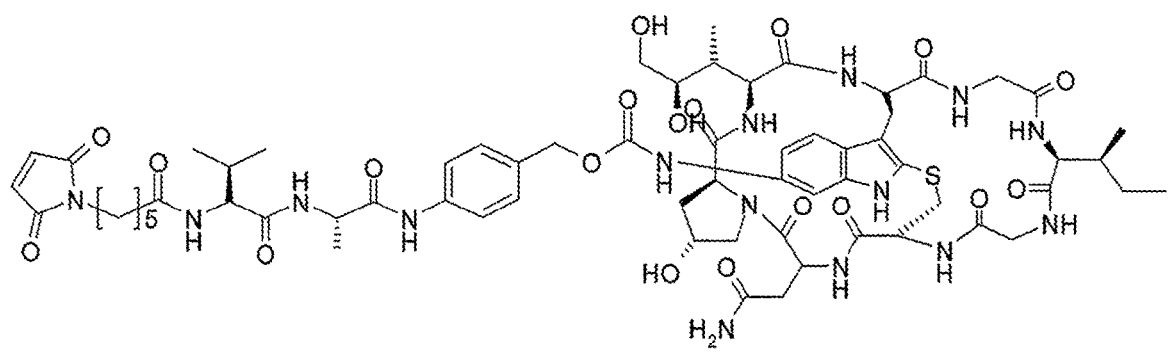
FIG. 5 shows a construct based on 6'.amino-amaninamide (HDP 30.2528) with a cleavable linker attached to the 6'-hydroxy group and a terminal maleimide group as an example of a reactive group Y for linking said construct to a target-binding moiety, and a corresponding 6'-hydroxy derivative (HDP 30.1699)
Figure 5:
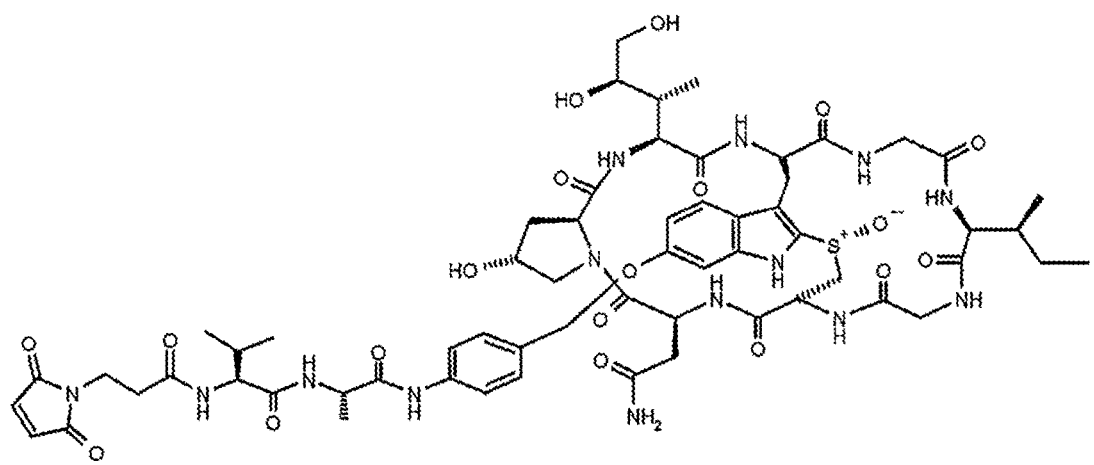
Figure 6A:
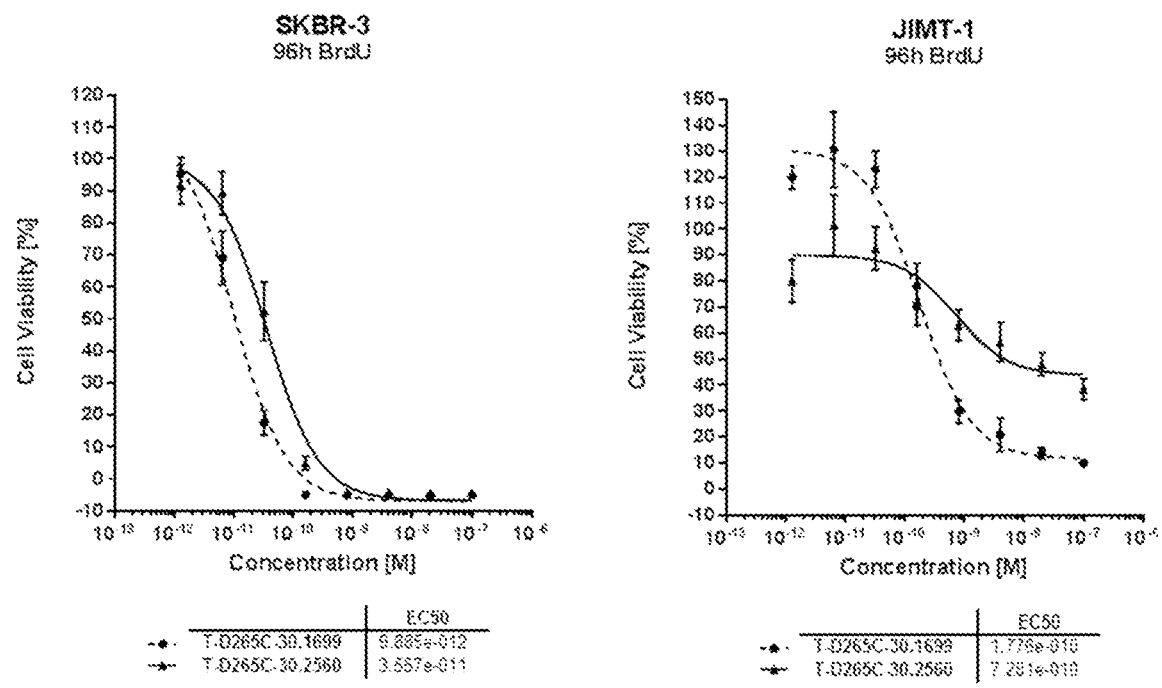
FIGS. 6A-6C show the cytotoxicity of HDP 30.2560 ADCs targeting (A) HER-2/neu on SKBR-3 cells (HER-2/ neu+++) and JIMT-1 cells (HER-2/neu+) (FIG. 6A), (B) PSMA on LnCap cells (PSMA+++) and 22rv1 cells (PSMA++) (FIG. 6A), and (C) CD19 on Raji cells (CD19+++) and Nalm-6 cells (CD19++) in comparison to HDP 30.1699 (FIG. 6C).
Figure 6B:
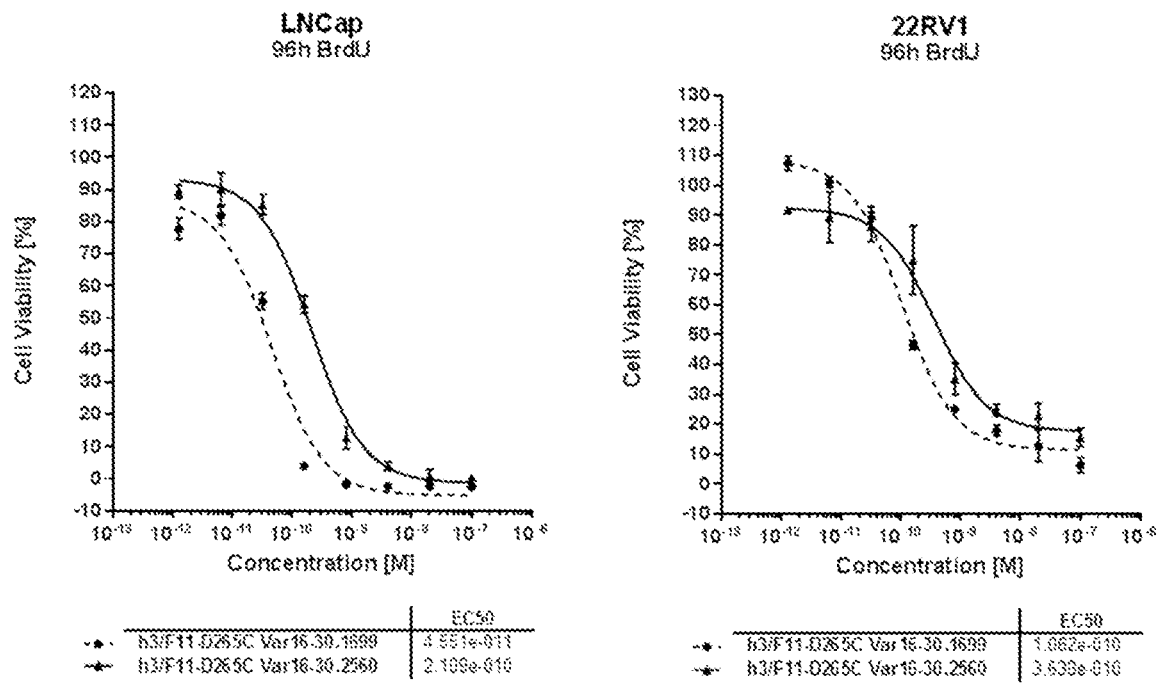
Figure 6C:
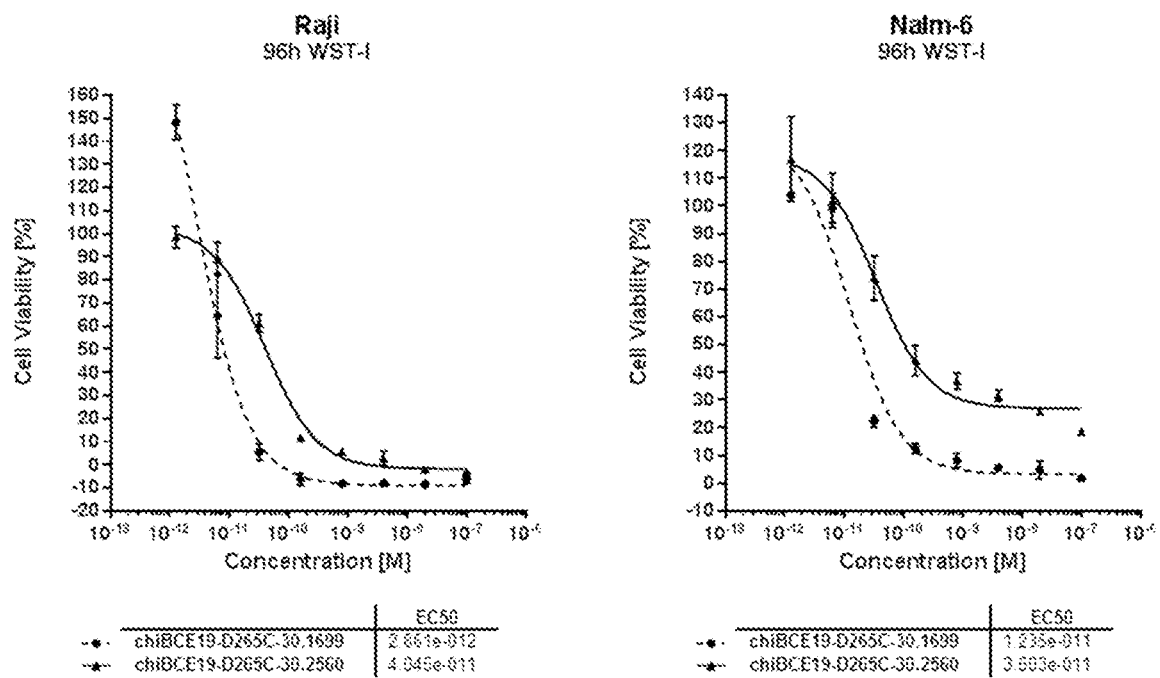

Functionally, amatoxins are defined as peptides or depsipeptides that inhibit mammalian RNA polymerase II. Preferred amatoxins are those with a functional group (e.g. a carboxylic group or carboxylic acid derivative such as a carboxamide or hydroxamic acid, an amino group, a hydroxy group, a thiol or a thiol-capturing group) that can be reacted with linker molecules or target-binding moieties as defined above. Amatoxins which are particularly suitable for the conjugates of the present invention are di-deoxy variants of α-amanitin, β-amanitin, γ-amanitin, ε-amanitin, amanullin, or amanullinic acid, or mono-deoxy variants of amanin, amaninamide, γ-amanin, or γ-amaninamide as shown in FIG. 1 as well as salts, chemical derivatives, semisynthetic analogues, and synthetic analogues thereof.

In a particular embodiment, the amino-substituted derivative, the amanitin derivative comprising an amino-substituted tryptophan moiety, and/or the conjugate of the present invention have/has a purity greater than 90%, particularly greater than 95%, more particularly greater than 98%, or even more than 99%.

In the context of the present invention, the term "purity" refers to the total amount of, e.g. conjugates being present. A purity of greater than 90%, for example, means that in 1 mg of a composition comprising a conjugate of the present invention, there are more than 90%, i.e. more than 900 μg, of such conjugate. The remaining part, i.e. the impurities may include unreacted starting material and other reactants, solvents, cleavage products and/or side products.

In a particular embodiment, a composition comprising the amino-substituted derivative, the amanitin derivative comprising an amino-substituted tryptophan moiety, and/or the conjugate of the present invention comprises more than 100 mg, in particular more than 500 mg, and more particularly more than 1 g of such amino-substituted derivative, amanitin derivative comprising an amino-substituted tryptophan moiety, and/or conjugate. Thus, trace amount of, e.g. a conjugate of the present invention that arguably may be present in complex preparations of conjugates of the prior art are explicitly excluded.

The term "target-binding moiety", as used herein, refers to any molecule or part of a molecule that can specifically bind to a target molecule or target epitope. Preferred target-binding moieties in the context of the present application are (i) antibodies or antigen-binding fragments thereof; (ii) antibody-like proteins; and (iii) nucleic acid aptamers. "Target-binding moieties" suitable for use in the present invention typically have a molecular mass of 40,000 Da (40 kDa) or more.

As used herein, a first compound (e.g. an antibody) is considered to "specifically bind" to a second compound (e.g. an antigen, such as a target protein), if it has a dissociation constant $K_D$ to said second compound of 100 μM or less, particularly 50 μM or less, particularly 30 μM or less, particularly 20 μM or less, particularly 10 μM or less, particularly 5 μM or less, more particularly 1 μM or less, more particularly 900 nM or less, more particularly 800 nM or less, more particularly 700 nM or less, more particularly 600 nM or less, more particularly 500 nM or less, more particularly 400 nM or less, more particularly 300 nM or less, more particularly 200 nM or less, even more particularly 100 nM or less, even more particularly 90 nM or less, even more particularly 80 nM or less, even more particularly 70 nM or less, even more particularly 60 nM or less, even more particularly 50 nM or less, even more particularly 40 nM or less, even more particularly 30 nM or less, even more particularly 20 nM or less, and even more particularly 10 nM or less.

In the context of the present application the terms "target molecule" and "target epitope", respectively, refers to an antigen and an epitope of an antigen, respectively, that is specifically bound by a target-binding moiety. Particularly the target molecule is a tumour-associated antigen, in particular an antigen or an epitope which is present on the surface of one or more tumour cell types in an increased concentration and/or in a different steric configuration as compared to the surface of non-tumour cells. Particularly, said antigen or epitope is present on the surface of one or more tumour cell types, but not on the surface of non-tumour cells. In particular embodiments, the target-binding moiety specifically binds to an epitope of an antigen selected from: PSMA, CD19, CD269, sialyl Lewis$^a$, HER-2/neu and epithelial cell adhesion molecule (EpCAM). In other embodiments, said antigen or epitope is preferentially expressed on cells involved in autoimmune diseases. In particular such embodiments, the target-binding moiety specifically binds to an epitope of the IL-6 receptor (IL-6R).

The term "antibody or antigen binding fragment thereof", as used herein, refers to immunoglobulin molecules and immunologically active portions of immunoglobulin molecules, i.e. molecules that contain an antigen-binding site that immunospecifically binds an antigen. Thus, the term "antigen-binding fragments thereof" refers to a fragment of an antibody comprising at least a functional antigen-binding domain. Also comprised are immunoglobulin-like proteins that are selected through techniques including, for example, phage display to specifically bind to a target molecule, e.g. to a target protein selected from: PSMA, CD19, CD269, sialyl Lewis$^a$, HER-2/neu and EpCAM. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. "Antibodies and antigen-binding fragments thereof" suitable for use in the present invention include, but are not limited to, polyclonal, monoclonal, monovalent, bispecific, heteroconjugate, multispecific, human, humanized (in particular CDR-grafted), deimmunized, or chimeric antibodies, single chain antibodies (e.g. scFv), Fab fragments, F(ab')2 fragments, fragments produced by a Fab expression library, diabodies or tetrabodies (Holliger P. et al., Proc Natl Acad Sci USA. 90 (1993) 6444-8), nanobodies, anti-idiotypic (anti-Id) antibodies (including, e.g., anti-Id antibodies to antibodies of the invention), and epitope-binding fragments of any of the above.

In some embodiments the antigen-binding fragments are human antigen-binding antibody fragments of the present invention and include, but are not limited to, Fab, Fab' and F(ab')$_2$, Fd, single-chain Fvs (scFv), single-chain antibodies, disulfide-linked Fvs (dsFv) and fragments comprising either a VL or VH domain. Antigen-binding antibody fragments, including single-chain antibodies, may comprise the variable domain(s) alone or in combination with the entirety or a portion of the following: hinge region, CL, CH1, CH2, and CH3 domains. Also included in the invention are antigen-binding fragments also comprising any combination of variable domain(s) with a hinge region, CL, CH1, CH2, and CH3 domains.

Antibodies usable in the invention may be from any animal origin including birds and mammals. Particularly, the antibodies are from human, rodent (e.g. mouse, rat, guinea pig, or rabbit), chicken, pig, sheep, goat, camel, cow, horse, donkey, cat, or dog origin. It is particularly preferred that the antibodies are of human or murine origin. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Particularly, the scaffold protein is a small globular protein. Antibody-like proteins include without limitation affibodies, anticalins, and designed ankyrin repeat proteins (for review see: Binz et al., Nat Biotechnol. 2005, 1257-68). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins.

The term "nucleic acid aptamer" refers to a nucleic acid molecule that has been engineered through repeated rounds of in vitro selection or SELEX (systematic evolution of ligands by exponential enrichment) to bind to a target molecule (for a review see: Brody and Gold, J Biotechnol. 74 (2000) 5-13). The nucleic acid aptamer may be a DNA or RNA molecule. The aptamers may contain modifications, e.g. modified nucleotides such as 2'-fluorine-substituted pyrimidines.

A "linker" in the context of the present invention refers to a structure that is connecting two components, each being attached to one end of the linker. In the case of the linker being a bond, a direct linkage of amatoxin to the antibody may decrease the ability of the amatoxin to interact with RNA polymerase II. In particular embodiments, the linker increases the distance between two components and alleviates steric interference between these components, such as in the present case between the antibody and the amatoxin. In particular embodiments, the linker has a continuous chain of between 1 and 30 atoms (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 atoms) in its backbone, i.e. the length of the linker is defined as the shortest connection as measured by the number of atoms or bonds between the amatoxin moiety and the antibody, wherein one side of the linker backbone has been reacted with the amatoxin and, the other side is available for reaction, or has been reacted, with an antibody. In the context of the present invention, a linker particularly is a $C_{1-20}$-alkylene, $C_{1-20}$-heteroalkylene, $C_{2-20}$-alkenylene, $C_{2-20}$-heteroalkenylene, $C_{2-20}$-alkynylene, $C_{2-20}$-heteroalkynylene, cycloalkylene, heterocycloalkylene, arylene, heteroarylene, aralkylene, or a heteroaralkylene group, optionally substituted. The linker may contain one or more structural elements such as carboxamide, ester, ether, thioether, disulfide, urea, thiourea, hydrocarbon moieties and the like. The linker may also contain combinations of two or more of these structural elements. Each one of these structural elements may be present in the linker more than once, e.g. twice, three times, four times, five times, or six times. In some embodiments the linker may comprise a disulfide bond. It is understood that the linker has to be attached either in a single step or in two or more subsequent steps to the amatoxin and the antibody. To that end the linker to be will carry two groups, particularly at a proximal and distal end, which can (i) form a covalent bond to a group present in one of the components to be linked, particularly an activated group on an amatoxin or the target binding-peptide or (ii) which is or can be activated to form a covalent bond with a group on an amatoxin. Accordingly, it is preferred that chemical groups are at the distal and proximal end of the linker, which are the result of such a coupling reaction, e.g. an ester, an ether, a urethane, a peptide bond etc.

In particular embodiments, the linker L is a linear chain of between 1 and 20 atoms independently selected from C, O, N and S, particularly between 2 and 18 atoms, more particularly between 5 and 16 atoms, and even more particularly between 6 and 15 atoms. In particular embodiments, at least 60% of the atoms in the linear chain are C atoms. In particular embodiments, the atoms in the linear chain are linked by single bonds.

In particular embodiments. the linker L is an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, comprising from 1 to 4 heteroatoms selected from N, O, and S, wherein said linker is optionally substituted.

The term "alkylene" refers to a bivalent straight chain saturated hydrocarbon groups having from 1 to 20 carbon atoms, including groups having from 1 to 10 carbon atoms. In certain embodiments, alkylene groups may be lower alkylene groups. The term "lower alkylene" refers to alkylene groups having from 1 to 6 carbon atoms, and in certain embodiments from 1 to 5 or 1 to 4 carbon atoms. Examples of alkylene groups include, but are not limited to, methylene ($-CH_2-$), ethylene ($-CH_2-CH_2-$), n-propylene, n-butylene, n-pentylene, and n-hexylene.

The term "alkenylene" refers to bivalent straight chain groups having 2 to 20 carbon atoms, wherein at least one of the carbon-carbon bonds is a double bond, while other bonds may be single bonds or further double bonds. The term "alkynylene" herein refers to groups having 2 to 20 carbon atoms, wherein at least one of the carbon-carbon bonds is a triple bond, while other bonds may be single, double or further triple bonds. Examples of alkenylene groups include ethenylene ($-CH{=}CH-$), 1-propenylene, 2-propenylene, 1-butenylene, 2-butenylene, 3-butenylene, and the like. Examples of alkynylene groups include ethynylene, 1-propynylene, 2-propynylene, and so forth.

As used herein, "cycloalkylene" is intended to refer to a bivalent ring being part of any stable monocyclic or polycyclic system, where such ring has between 3 and 12 carbon atoms, but no heteroatom, and where such ring is fully saturated, and the term "cycloalkenylene" is intended to refer to a bivalent ring being part of any stable monocyclic or polycyclic system, where such ring has between 3 and 12 carbon atoms, but no heteroatom, and where such ring is at least partially unsaturated (but excluding any arylene ring). Examples of cycloalkylenes include, but are not limited to, cyclopropylene, cyclobutylene, cyclopentylene, cyclohexylene, and cycloheptylene. Examples of cycloalkenylenes include, but are not limited to, cyclopentenylene and cyclohexenylene.

As used herein, the terms "heterocycloalkylene" and "heterocycloalkenylene" are intended to refer to a bivalent ring being part of any stable monocyclic or polycyclic ring system, where such ring has between 3 and about 12 atoms, and where such ring consists of carbon atoms and at least one heteroatom, particularly at least one heteroatom independently selected from the group consisting of N, O and S, with heterocycloalkylene referring to such a ring that is fully saturated, and heterocycloalkenylene referring to a ring that is at least partially unsaturated (but excluding any arylene or heteroarylene ring).

The term "arylene" is intended to mean a bivalent ring or ring system being part of any stable monocyclic or polycyclic system, where such ring or ring system has between 3 and 20 carbon atoms, but has no heteroatom, which ring or ring system consists of an aromatic moiety as defined by the "4n+2" π electron rule, including phenylene.

As used herein, the term "heteroarylene" refers to a bivalent ring or ring system being part of any stable mono- or polycyclic system, where such ring or ring system has between 3 and 20 atoms, which ring or ring system consists of an aromatic moiety as defined by the "4n+2" π electron rule and contains carbon atoms and one or more nitrogen, sulfur, and/or oxygen heteroatoms.

In the context of the present invention, the term "substituted" is intended to indicate that one or more hydrogens present in the backbone of a linker is replaced with a selection from the indicated group(s), provided that the indicated atom's normal valency, or that of the appropriate atom of the group that is substituted, is not exceeded, and that the substitution results in a stable compound. The term "optionally substituted" is intended to mean that the linker is either unsubstituted or substituted, as defined herein, with one or more substituents, as defined herein. When a substituent is a keto (or oxo, i.e. $=O$) group, a thio or imino group or the like, then two hydrogens on the linker backbone atom are replaced. Exemplary substituents include, for example, alkyl, alkenyl, alkynyl, cycloalkyl, heterocycloalkyl, aryl, heteroaryl, aralkyl, heteroaralkyl, acyl, aroyl, heteroaroyl, carboxyl, alkoxy, aryloxy, acyloxy, aroyloxy, heteroaroyloxy, alkoxycarbonyl, halogen, (thio)ester, cyano, phosphoryl, amino, imino, (thio)amido, sulfhydryl, alkylthio, acylthio, sulfonyl, a sulfate, a sulfonate, a sulfamoyl, a sulfonamido, nitro, azido, haloalkyl, including perfluoroalkyl (such as trifluoromethyl), haloalkoxy, alkylsulfanyl, alkylsulfinyl, alkylsulfonyl, alkylsulfonylamino, arylsulfonoamino, phosphoryl, phosphate, phosphonate, phosphinate, alkylcarboxy, alkylcarboxyamide, oxo, hydroxy, mercapto, amino (optionally mono- or di-substituted, e.g. by alkyl, aryl, or heteroaryl), imino, carboxamide, carbamoyl (optionally mono- or di-substituted, e.g. by alkyl, aryl, or heteroaryl), amidino, aminosulfonyl, acylamino, aroylamino, (thio)ureido, (arylthio)ureido, alkyl(thio)ureido, cycloalkyl(thio)ureido, aryloxy, aralkoxy, or $-O(CH_2)_n-OH$, $-O(CH_2)_n-NH_2$, $-O(CH_2)_nCOOH$, $-(CH_2)_nCOOH$, $-C(O)O(CH_2)_nR$, $-(CH_2)_nN(H)C(O)OR$, or $-N(R)S(O)_2R$ wherein n is 1-4 and R is independently selected from hydrogen, -alkyl, -alkenyl, -alkynyl, -cycloalkyl, -cycloalkenyl, —(C-linked-heterocycloalkyl), —(C-linked-heterocycloalkenyl), -aryl, and -heteroaryl, with multiple degrees of substitution being allowed. It will be understood by those skilled in the art that substituents, such as heterocycloalkyl, aryl, heteroaryl, alkyl, etc., or functional groups such as —OH, —NHR etc., can themselves be substituted, if appropriate. It will also be understood by those skilled in the art that the substituted moieties themselves can be substituted as well when appropriate.

In particular embodiments, the linker L comprises a moiety selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—).

In particular embodiments of the present invention, the linker L comprises a number of m groups selected from the list of: alkylene, alkenylene, alkynylene, cycloalkylene, heteroalkylene, heteroalkenylene, heteroalkynylene, heterocycloalkylene, arylene, heteroarylene, aralkylene, and a heteroaralkylene group, wherein each group may optionally be independently substituted, the linker further comprises a number of n moieties independently selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—), wherein m=n+1. In particular embodiments, m is 2 and n is 1, or m is 3 and n is 2. In particular embodiments, the linker comprises 2 or 3 unsubstituted alkylene groups, and 1 or 2, respectively, disulfide, ether, thioether, amine, ester, carboxamide, urethane or urea moieties linking the unsubstituted alkylene groups.

In a particular embodiment, the linker L does not comprise a heteroarylene group.

In particular embodiments, the C atoms in the linear chain are independently part of optionally substituted methylene groups (—CH$_2$—). In particular such embodiments, the optional substituents are independently selected from halogen and C$_{1-6}$-alkyl, particularly methyl.

In particular embodiments, the linker L is a stable linker.

In the context of the present invention, the term "stable linker" refers to a linker that is stable (i) in the presence of enzymes, and (ii) in an intracellular reducing environment.

In particular embodiments, the stable linker does not contain (i) an enzyme-cleavable substructure, and/or (ii) a disulfide group. In particular such embodiments, the linker has a length of up to 12 atoms, particularly from 2 to 10, more particularly from 4 to 9, and most particularly from 6 to 8 atoms.

In particular other embodiments, the linker is a cleavable linker.

In the context of the present invention, the term "cleavable linker" refers to a linker that is (i) cleavable by an enzyme, or (ii) a reducible linker. In particular embodiments, the term only refers to a linker that is cleavable by an enzyme (not to a reducible linker).

In the context of the present invention, the term "linker that is cleavable . . . by an enzyme" refers to a linker that can be cleaved by an enzyme, particularly by a lysosomal peptidase, such as Cathepsin B, resulting in the intracellular release of the toxin cargo conjugated to the targeting antibody after internalization (see Dubowchik et al., Bioconjug Chem. 13 (2002) 855-69). In particular embodiments, the cleavable linker comprises a dipeptide selected from: Phe-Lys, Val-Lys, Phe-Ala, Val-Ala, Phe-Cit and Val-Cit, particularly wherein the cleavable linker further comprises a p-aminobenzyl (PAB) spacer between the dipeptides and the amatoxin.

In particular such embodiments, the cleavable linker comprises a structure L$^1$-L*-L$^2$, wherein L* is p-aminobenzyl dipeptide moiety, L$^1$ is a part of the linker that connects L* to the amatoxin, in particular, wherein L$^1$ is connected to L* via a —NH— or a —O— group, particularly a —C(=O)—NH—, a —C(=O)—NH—O— or a —C(=O)—O— group, and wherein L$^2$ is a part of the linker that connects L* to the target-binding moiety, in particular wherein L$^2$ is connected to L* via a —(CH$_2$)$_m$— moiety, with m being an integer selected from 1 to 8, in particular from 1 to 5, or via a —(CH$_2$ CH$_2$O)$_n$— moiety, with n being an integer selected from 1 to 3, in particular from 1 to 2. For example, in the case of the cleavable linker comprising the dipeptide Val-Ala, the structure of L$^1$-L*-L$^2$ is as follows:

L$^1$—L*—L$^2$

In particular other such embodiments, L* comprises the dipeptide Val-Lys and has the following structure:

In particular embodiments, the linker L$^1$ is a linear chain of between 1 and 4 atoms independently selected from C, O, N and S, particularly between 1 and 3 atoms, more particularly between 1 and 2 atoms, and even more just 1 atom. In particular embodiments, at least 50% of the atoms in the linear chain are C atoms. In particular embodiments, the atoms in the linear chain are linked by single bonds.

In a particular embodiment, L$^1$ is an —NH— or an —O— group that is part of the amatoxin. In particular embodiments, L$^1$ is an —NH— group originating from the amino group attached to position 6' of the central tryptophan moiety in accordance with the present invention. In particular embodiments, L$^1$ is an —O— group originating from the hydroxyl group being part of the carboxylic acid group of amino acid residue 1 of an amanine derivative according to the present invention. In particular embodiments, L$^1$ is an —NH— group originating from the amino group being part of the carboxamide group of amino acid residue 1 of an amanineamide derivative according to the present invention. In particular embodiments, L$^1$ is an —O— group originating from a hydroxyl group being part of amino acid residue 3 of an amanin or amanineamide derivative according to the present invention.

In the context of the present invention, the term "reducible linker" refers to a linker that can be cleaved in the intracellular reducing environment, particularly a linker that contains a disulfide groups, resulting in the intracellular release of the toxin cargo conjugated to the target-binding moiety after internalization by the intracellular reducing environment (see Shen et al., J. Biol. Chem. 260 (1985) 10905-10908). In particular embodiments, the reducible linker comprises a moiety

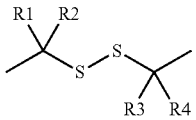

wherein R1 to R4 are independently selected from H and methyl.

In particular such embodiments, such cleavable linker has a length of up to 20 atoms, particularly from 6 to 18, more particularly from 8 to 16, and most particularly from 10 to 15 atoms. In particular such embodiments, the part of the linker linking the amatoxin according to the present invention and the cleavable disulfide group is a linear chain of 3 or 4 C atoms, particularly 3 C atoms. In particular embodiments, the 3 or 4 C atoms in the linear chain are linked by single bonds. In particular embodiments, the linker is an n-propylene group.

In particular embodiments, said linker is present and is connected on one side to the amino group attached to the phenyl ring of the central tryptophan moiety, i. e. to the 6'-amino substituent.

In particular other embodiments, said linker is present and is connected on one side to a position in the amanitin derivative of the present invention, wherein said position is selected from (i) in the case of S-desoxy-6'-amino-amaninamide or 6'-amino-amaninamide, the nitrogen atom of the amide group at the γ C-atom of amatoxin amino acid 1 (amide linkage);

(ii) in the case of S-desoxy-6'-amino-amanin or 6'-amino-amanin, the oxygen atom of the acid group at the γ C-atom of amatoxin amino acid 1 (ester linkage);

(iii) in the case of a derivative of the amanitin of the present invention, wherein the free carboxylic acid moiety of amino acid 1 has been converted to a moiety —C(═O)NH—OR1, the oxygen atom of the hydroxamic acid group at the γ C-atom of amatoxin amino acid 1;

(iv) the oxygen atom of the hydroxy group at the δ C-atom of amatoxin amino acid 3, particularly via an ester linkage, an ether linkage or a urethane linkage; or (v) the ring nitrogen of amino acid 4.

Coupling of the linker to the target-binding moiety can be achieved by a variety of methods well known to one of ordinary skill in the art, particularly in the art of antibody-drug conjugates (ADCs).

In particular embodiments, said linker is connected to the target-binding moiety via a urea moiety ( . . . -linker-NH—C(═O)—NH-target-binding moiety). In particular such embodiments, the urea moiety results from a reaction of a primary amine originally present in the target-binding moiety, such as an amino group of a lysine side chain, with a carbamic acid derivative . . . -linker-NH—C(O)—Z, wherein Z is a leaving group that can be replaced by a primary amine.

In particular other embodiments, said linker is present and is connected to the target-binding moiety via a thioether moiety ( . . . -linker-S-target-binding moiety). Thus, in such embodiments, the present invention relates to a conjugate of generic formula:

Amanitin-L-X-S-Tbm, wherein Amanitin is an amanitin derivative according to the present invention, L is a linker, X* is a moiety resulting from coupling of a thiol group to a thiol-reactive group, S is the sulphur atom of said thiol group, particularly the thiol group of a cysteine amino acid residue, and Tbm is a target-binding moiety, particularly an antibody or a functional antibody fragment comprising said cysteine amino acid residue. In particular embodiments, said cysteine amino acid residue (i) is located in an antibody domain selected from CL, CH1, CH2, and CH3; (ii) is located at a position, where the germline sequence exhibiting the closest homology to the sequence of said antibody domain contains an amino acid residue different from cysteine; and (iii) is located a position that is solvent-exposed.

In the context of the present invention, the term "thiol-reactive group" refers to a group that selectively reacts with the thiol group of, for example, a free cysteine of an antibody, particularly in a pH value in the range between 6.0 and 8.0, more particularly in a pH value in the range between 6.5 and 7.5. In particular, the term "selectively" means that less than 10% of the coupling reactions of a molecule comprising a thiol-reactive group with an antibody comprising at least one free cysteine residue are coupling reactions with non-cysteine residues of the antibody, such as lysine residues, particularly less than 5%, more particularly less than 2%. In particular embodiments, the thiol-reactive group is selected from bromoacetamide, iodoacetamide, maleimide, a maleimide having a leaving group in position 3, in particular a leaving group selected from —Br, and substituted thiol (see, for example, U.S. Pat. No. 9,295,729), a 1,2-dihydropyridazine-3,6-dione having a leaving group in position 4, in particular a leaving group selected from —Br, and substituted thiol (see, for example, U.S. Pat. No. 9,295,729), methylsulfonyl benzothiazole, methylsulfonyl phenyltetrazole, methylsulfonyl phenyloxadiazole (see Toda et al., Angew. Chem. Int. Ed. Engl., 52 (2013) 12592-6), a 3-arylpropionitrile (see Kolodych et al, Bioconjugate Chem. 2015, 26, 197-200), and 5-nitro-pyridin-2-yl-disulfide ( . . . -L-S—S-(5-nitro-pyridine-2-yl).

In particular embodiments, said position or functional group, which is on one side connected to the linker and which can directly or indirectly be connected to a position or functional group present in a target-binding moiety is a moiety that can react with two thiol groups present in one target-binding moiety or in two target-binding moieties. In particular embodiments, the thiol-reactive groups is a maleimide having two leaving groups in positions 3 and 4, in particular selected from 3,4-dibromomaleimide, 3,4-bis(arylthio)-maleimide, in particular 3,4-diphenylthio-maleimide, and 3,4-bis(heteroarylthio)-maleimide, in particular 3,4-bis(2-pyridinyl-sulfanyl)-maleimide, and. In particular other embodiments, the thiol-reactive groups is a 1,2-dihydropyridazine-3,6-dione having two leaving groups in positions 4 and 5, in particular selected from 4,5-bromo-1,2-dihydropyridazine-3,6-dione, 4,5-bis(arylthio)-1,2-dihydropyridazine-3,6-dione, in particular 4,5-diphenylthio-1,2-dihydropyridazine-3,6-dione, and 4,5-bis(heteroarylthio)-1,2-dihydropyridazine-3,6-dione, in particular 4,5-bis(2-pyridinyl-sulfanyl)-1,2-dihydropyridazine-3,6-dione.

In particular embodiments, the moiety resulting from coupling of a thiol group to a thiol-reactive group is selected from: thiol-substituted acetamide; thiol-substituted succinimide; thiol-substituted succinamic acid; thiol-substituted heteroaryl, particularly thiol-substituted benzothiazole, thiol-substituted phenyltetrazole and thiol-substituted phenyloxadiazole; and a disulphide, wherein one sulphur atom is derived from a cysteine residue of the antibody. In particular embodiments, the moiety resulting from coupling of a thiol group to a thiol-reactive group is a thiol-substituted succinimide.

In particular embodiments, the linker L in the moiety L-X*-S present in the generic formula of section [0092], is selected from the following group of moieties:

(Amanitin side) —(CH$_2$)$_2$—S—S—(CH$_2$)$_2$—X—S— (Tbm side);
(Amanitin side) —(CH$_2$)$_3$—S—S—(CH$_2$)$_2$—X—S— (Tbm side);
(Amanitin side) —(CH$_2$)$_2$—S—S—(CH$_2$)$_3$—X—S— (Tbm side);
(Amanitin side) —(CH$_2$)$_3$—S—S—(CH$_2$)$_3$—X—S— (Tbm side);
(Amanitin side) —(CH$_2$)$_4$—S—S—(CH$_2$)$_4$—X—S— (Tbm side);
(Amanitin side) —(CH$_2$)$_2$—CMe$_2$-S—S—(CH$_2$)$_2$—X—S— (Tbm side);
(Amanitin side) —(CH$_2$)$_2$—S—S—CMe$_2$-(CH$_2$)$_2$—X—S— (Tbm side);
(Amanitin side) —(CH$_2$)$_3$—S—S— (Tbm side);
(Amanitin side) —CH$_2$-C$_6$H$_4$—NH-Cit-Val-CO(CH$_2$)$_5$—X—S— (Tbm side)
(Amanitin side) —CH$_2$-C$_6$H$_4$—NH-Ala-Val-CO(CH$_2$)$_5$—X—S— (Tbm side);
(Amanitin side) —CH$_2$-C$_6$H$_4$—NH-Ala-Val-CO(CH$_2$)$_2$—X—S— (Tbm side);
(Amanitin side) —CH$_2$-C$_6$H$_4$—NH-Ala-Phe-CO(CH$_2$)$_2$—X—S— (Tbm side);
(Amanitin side) —CH$_2$-C$_6$H$_4$—NH-Lys-Phe-CO(CH$_2$)$_2$—X—S— (Tbm side);
(Amanitin side) —CH$_2$-C$_6$H$_4$—NH-Cit-Phe-CO(CH$_2$)$_2$—X—S— (Tbm side);
(Amanitin side) —CH$_2$-C$_6$H$_4$—NH-Val-Val-CO(CH$_2$)$_2$—X—S— (Tbm side);
(Amanitin side) —CH$_2$-C$_6$H$_4$—NH-Ile-Val-CO(CH$_2$)$_2$—X—S— (Tbm side);
(Amanitin side) —CH$_2$-C$_6$H$_4$—NH-His-Val-CO(CH$_2$)$_2$—X—S— (Tbm side);
(Amanitin side) —CH$_2$-C$_6$H$_4$—NH-Met-Val-CO(CH$_2$)$_2$—X—S— (Tbm side);
(Amanitin side) —CH$_2$-C$_6$H$_4$—NH-Asn-Lys-CO(CH$_2$)$_2$—X—S— (Tbm side); and
wherein —NH— and —CO— flanking the dipeptide sequences represent amino and carbonyl moieties of the linker forming amide bonds to the carboxy- and the amino-terminus of the dipeptide, respectively.

In the context of the present invention, the term "a moiety resulting from coupling of a thiol group to a thiol-reactive group" refers to a structure that results from (i) the nucleophilic substitution of a leaving group Y present in a thiol-reactive group by the sulphur atom of a cysteine residue, for example a bromo acetamide group, a iodo acetamide, a 4,6-dichloro-1,3,5-triazin-2-ylamino group, an alkylsulfone or a heteroarylsulfone; (ii) the addition of the HS-group of a cysteine residue to an activated double bond of a thiol-reactive group, for example maleimide, or (iii) an disulfide exchange of an activated disulfide or methanethiosulfonate with the sulphur atom of a cysteine residue, for example with pyridine-2-thiol, 5-nitropyridine-2-thiol or methanesulfinate as leaving group; or (iv) any other chemical reaction that results in a stable bond between the sulphur atom of a cysteine residue and a reactive moiety being part of the thiol-reactive group.

The primary moiety resulting from coupling of thiol group may be optionally further derivatized, e.g. the succinimidyl thioether resulting from a maleimide can be hydrolysed to succinamic acid thioethers of the following generic structures

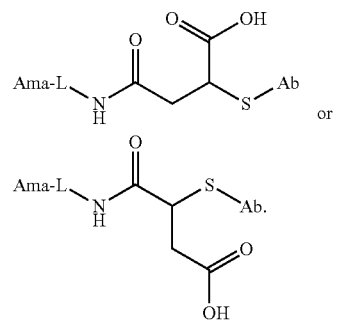

In particular other embodiments, site-specific coupling can be achieved by reducing a disulfide bridge present in the target-binding moiety, and by reacting the two cysteine residues with a bridging moiety X* present in an Amanitin-L-X* construct (see Badescu et al. Bridging disulfides for stable and defined antibody drug conjugates. Bioconjugate Chemistry. 25 (2014) 1124-1136).

In a similar embodiment, site-specific coupling can be achieved by reducing a disulfide bridge present in the target-binding moiety, and by reacting the two cysteine residues with a bridging moiety X* present in a Amanitin-L-X* construct, particularly wherein X* is

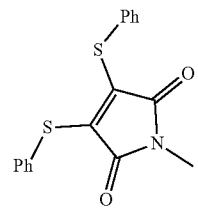

(see Bryden et al., Bioconjug Chem, 25 (2014) 611-617; Schumacher et al., Org Biomol Chem, 2014, 7261-7269)

In a particular other embodiment, coupling is achieved by regiospecific coupling of an amino group present in the linker to a glutamine residue present in the target-binding moiety via a transaminase, particularly by coupling to glutamine Q295 of an antibody.

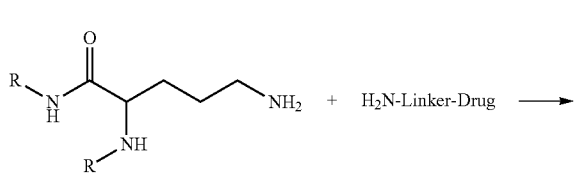

-continued

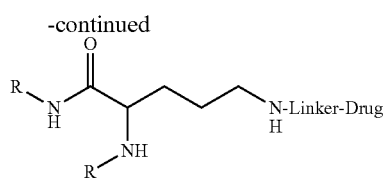

In a particular embodiment, coupling is achieved by site-specific conjugation to target-binding moieties comprising N-glycan side chains. In particular, the N-glycan side chain can be degraded enzymatically, followed by trans-glycosylation with an azido-galactose. Using click chemistry, such modified target-binding moiety can be coupled to appropriately modified constructs Amanitin -L-X*, wherein X* is, for example, a dibenzo-cyclooctyne (DIBO) or an analogous moiety comprising a C—C triple bond. For example, a construct Amanitin -L-$NH_2$ can be coupled to DIBO-SE

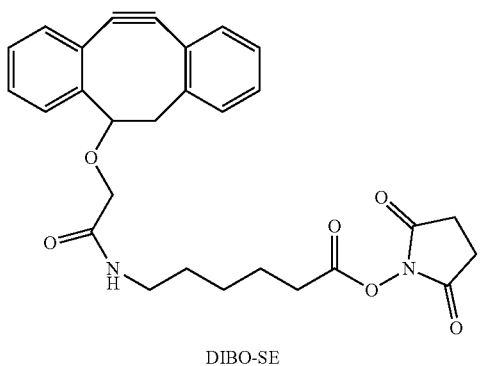 [SMILES: O=C(COC1Cc2ccccc2C#Cc2ccccc21)NCCCCCC(=O)ON1C(=O)CCC1=O]

DIBO-SE by nucleophilic substitution of the hydroxy succinimide moiety. The resulting DIBO-modified linker construct can then be coupled to the azido derivative mentioned above. In an alternative embodiment, the target-binding moiety can be modified by incorporation of a non-natural amino acid that permits click-chemistry, in particular by incorporation of a para-azidomethyl-L-phenylalanine (pAMF).

In particular embodiments, the linker L in -L-X* is a linear chain of at least 5, particularly at least 10, more particularly between 10 and 20 atoms independently selected from C, O, N and S, particularly between 10 and 18 atoms, more particularly between 10 and 16 atoms, and even more particularly between 10 and 15 atoms. In particular embodiments, at least 60% of the atoms in the linear chain are C atoms. In particular embodiments, the atoms in the linear chain are linked by single bonds.

In alternative embodiments, the position or functional group, which can directly or indirectly be connected to a position or functional group present in a target-binding moiety, is not an ethynyl group, or, more generally, is not an alkynyl group, or is not a group that can be reacted with an 1,3 dipole in a 1,3-dipolar cycloaddition (click chemistry).

In particular other embodiments, site-specific coupling of a Amanitin -L-X* construct to a target-binding moiety can be achieved by incorporation of a non-natural amino acid comprising a keto group, in particular p-acetylphenylalanine (pAcPhe), into the target-binding moiety, and by reacting such modified target-binding moiety with an Amanitin -L-X* construct, wherein X* is a hydroxylamine moiety.

In a further embodiment, a formyl group can be introduced by formylglycine generating enzyme (FGE), which is highly selective for a cysteine group in a recognition sequence CxPxR to generate an aldehyde tag. Such aldehyde tag can be reacted with an appropriate group X* present in an Amanitin -L-X* construct, in particular wherein X* is 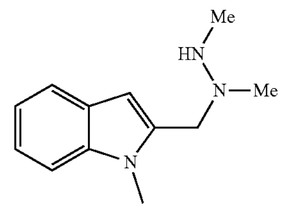 (see Agarwal et al., Bioconjugate Chem 24 (2013) 846-851).

In a second aspect, the present invention relates to a pharmaceutical composition comprising the conjugate of the present invention.

In a third aspect, the present invention relates to a conjugate of the present invention for use in the treatment of cancer in a patient, particularly wherein the cancer is selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, leukemia, and malignant lymphoma.

As used herein, “treat”, “treating” or “treatment” of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the treatment may comprise administering a conjugate or a pharmaceutical composition according to the present invention to a patient, wherein “administering” includes in vivo administration, as well as administration directly to tissue ex vivo, such as vein grafts.

In particular embodiments, a therapeutically effective amount of the conjugate of the present invention is used.

A “therapeutically effective amount” is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

In another aspect the present invention relates to pharmaceutical composition comprising an amanitin derivative according to the present invention, or a conjugate of the present invention of an amanitin derivative with a target-binding moiety, and further comprising one or more pharmaceutically acceptable diluents, carriers, excipients, fillers, binders, lubricants, glidants, disintegrants, adsorbents; and/or preservatives.

“Pharmaceutically acceptable” means approved by a regulatory agency of the Federal or a state government or listed in the U.S. Pharmacopeia or other generally recognized pharmacopeia for use in animals, and more particularly in humans.

In particular embodiments, the pharmaceutical composition is used in the form of a systemically administered medicament. This includes parenterals, which comprise among others injectables and infusions. Injectables are formulated either in the form of ampoules or as so called ready-for-use injectables, e.g. ready-to-use syringes or single-use syringes and aside from this in puncturable flasks for multiple withdrawal. The administration of injectables can be in the form of subcutaneous (s.c.), intramuscular (i.m.), intravenous (i.v.) or intracutaneous (i.c.) application. In particular, it is possible to produce the respectively suitable injection formulations as a suspension of crystals, solutions, nanoparticular or a colloid dispersed systems like, e.g. hydrosols.

Injectable formulations can further be produced as concentrates, which can be dissolved or dispersed with aqueous isotonic diluents. The infusion can also be prepared in form of isotonic solutions, fatty emulsions, liposomal formulations and micro-emulsions. Similar to injectables, infusion formulations can also be prepared in the form of concentrates for dilution. Injectable formulations can also be applied in the form of permanent infusions both in in-patient and ambulant therapy, e.g. by way of mini-pumps.

It is possible to add to parenteral drug formulations, for example, albumin, plasma, expander, surface-active substances, organic diluents, pH-influencing substances, complexing substances or polymeric substances, in particular as substances to influence the adsorption of the target-binding moiety toxin conjugates of the invention to proteins or polymers or they can also be added with the aim to reduce the adsorption of the target-binding moiety toxin conjugates of the invention to materials like injection instruments or packaging-materials, for example, plastic or glass.

The amanitin derivatives of the present invention comprising a target-binding moiety can be bound to microcarriers or nanoparticles in parenterals like, for example, to finely dispersed particles based on poly(meth)acrylates, polylactates, polyglycolates, polyamino acids or polyether urethanes. Parenteral formulations can also be modified as depot preparations, e.g. based on the "multiple unit principle", if the target-binding moiety toxin conjugates of the invention are introduced in finely dispersed, dispersed and suspended form, respectively, or as a suspension of crystals in the medicament or based on the "single unit principle" if the target-binding moiety toxin conjugate of the invention is enclosed in a formulation, e.g. in a tablet or a rod which is subsequently implanted. These implants or depot medicaments in single unit and multiple unit formulations often consist of so called biodegradable polymers like e.g. polyesters of lactic acid and glycolic acid, polyether urethanes, polyamino acids, poly(meth)acrylates or polysaccharides.

Adjuvants and carriers added during the production of the pharmaceutical compositions of the present invention formulated as parenterals are particularly aqua sterilisata (sterilized water), pH value influencing substances like, e.g. organic or inorganic acids or bases as well as salts thereof, buffering substances for adjusting pH values, substances for isotonization like e.g. sodium chloride, sodium hydrogen carbonate, glucose and fructose, tensides and surfactants, respectively, and emulsifiers like, e.g. partial esters of fatty acids of polyoxyethylene sorbitans (for example, Tween®) or, e.g. fatty acid esters of polyoxyethylenes (for example, Cremophor®), fatty oils like, e.g. peanut oil, soybean oil or castor oil, synthetic esters of fatty acids like, e.g. ethyl oleate, isopropyl myristate and neutral oil (for example, Miglyol®) as well as polymeric adjuvants like, e.g. gelatine, dextran, polyvinylpyrrolidone, additives which increase the solubility of organic solvents like, e.g. propylene glycol, ethanol, N,N-dimethylacetamide, propylene glycol or complex forming substances like, e.g. citrate and urea, preservatives like, e.g. benzoic acid hydroxypropyl ester and methyl ester, benzyl alcohol, antioxidants like e.g. sodium sulfite and stabilizers like e.g. EDTA.

When formulating the pharmaceutical compositions of the present invention as suspensions in a preferred embodiment thickening agents to prevent the setting of the target-binding moiety toxin conjugates of the invention or, tensides and polyelectrolytes to assure the resuspendability of sediments and/or complex forming agents like, for example, EDTA are added. It is also possible to achieve complexes of the active ingredient with various polymers. Examples of such polymers are polyethylene glycol, polystyrene, carboxymethyl cellulose, Pluronics® or polyethylene glycol sorbit fatty acid ester. The target-binding moiety toxin conjugates of the invention can also be incorporated in liquid formulations in the form of inclusion compounds e.g. with cyclodextrins. In particular embodiments dispersing agents can be added as further adjuvants. For the production of lyophilisates scaffolding agents like mannite, dextran, saccharose, human albumin, lactose, PVP or varieties of gelatine can be used.

EXAMPLES

In the following, the invention is explained in more detail by non-limiting examples:

Total synthesis of 6'-amino-amaninamide (HDP 30.2528)

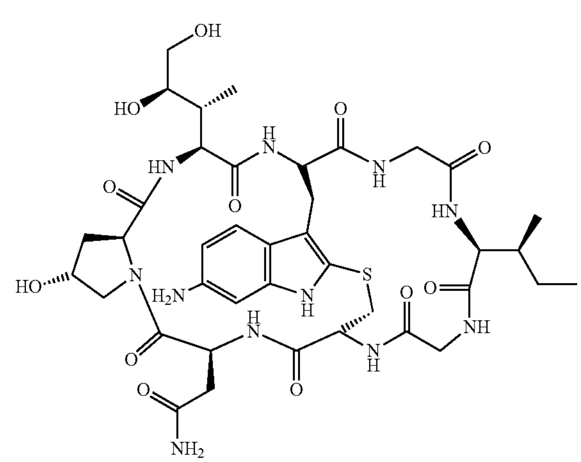

HDP 30.2528

1. Preparation of N-(tert-butoxycarbonyl)-6-nitro-L-tryptophan HDP 30.2353

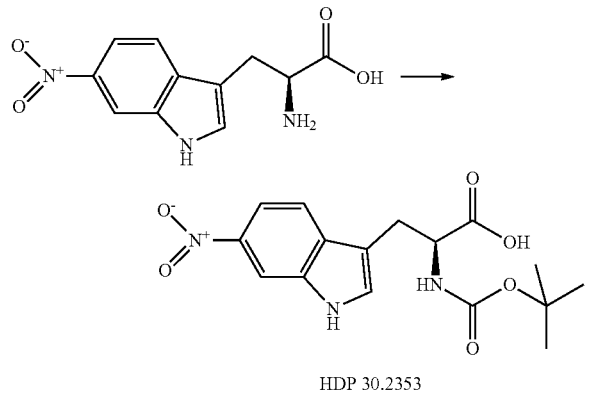

HDP 30.2353

9.0 g (28.8 mmol) 6-Nitro-L-tryptophan (prepared according to Hu, Weimin; Zhang, Fengying; Xu, Zhengren; Liu, Qiang; Cui, Yuxin; Jia, Yanxing Organic Letters Volume 12 Issue 5 Pages 956-959 Journal 2010) was suspended in a mixture of 60 ml 1,4-dioxane and 30 ml water. Under argon 57.7 ml (57.7 mmol) 1 N NaOH were added at ambient temperature. The resulting solution was cooled in an ice bath to 0° C. and treated with 7.3 ml (6.9 g; 31.7 mmol) Boc anhydride ($Boc_2O$). The mixture was stirred for 2.5 hours at room temperature and acidified with 1 N $KHSO_4$-solution to pH 3.0 by using a pH-meter. The aqueous phase was extracted three times with 75 ml ethylacetate. The combined organic extracts were washed with saturated NaCl solution and dried over $MgSO_4$. Filtration and evaporation to dryness gave 9.7 g crude material. The crude N-Boc-6-nitro-L-tryptophan was purified by flash chromatography on a 330 g silica gel column (detection wave length 254 nm) with a gradient of $CHCl_3$+1% acetic acid to $CHCl_3$/MeOH (9:1)+ 1% acetic acid and gave after evaporation and co-evaporation with toluene 3.8 g (38%) HDP 30.2353 as a white solid.

MS (ESI⁻) found: 348.07[M−H]⁻; calc.: 348.12 ($C_{16}H_{18}N_3O_6$)

2. Preparation of N-(tert-butoxycarbonyl)-6-amino-L-tryptophan HDP 30.2375

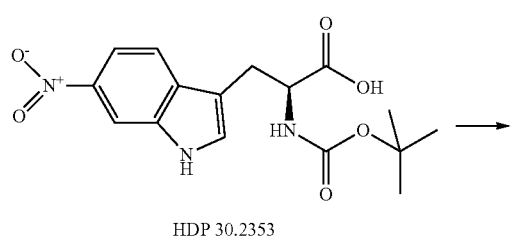

HDP 30.2353

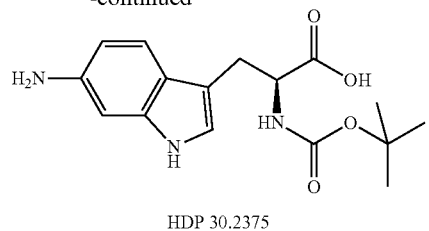

HDP 30.2375

6.9 g (19.9 mmol) N-(tert-butoxycarbonyl)-6-nitro-L-tryptophan HDP 30.2353 were dissolved in 250 ml methanol. 1.7 g 10% palladium on carbon were added and the mixture was hydrogenated 19 hours with hydrogen at ambient temperature and 1 bar. The catalyst was filtered off and the solution was evaporated to dryness. The crude product was a beige coloured solid which was used for the next step without further purification.

5.6 g (89.0% yield)

MS (ESI) found: 321.23[M+1]⁺; calc.: 320.16 ($C_{16}H_{22}N_3O_4$)

3. Preparation of N-(tert-butoxycarbonyl)-L-6-trifluoroacetamino-tryptophan HDP 30.2381

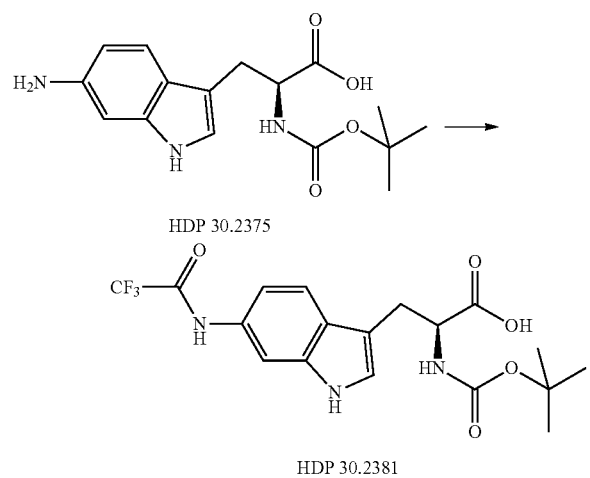

HDP 30.2381

4.5 g (14.2 mmol) N-(tert-butoxycarbonyl)-6-amino-L-tryptophan HDP 30.2375 were suspended in 45 ml dry tetrahydrofuran. Under argon 12.0 ml (14.4 g, 101.1 mmol) trifluoroacetic-acid-ethylester and 174 mg dimethylamino pyridine (DMAP) were added at ambient temperature. The resulting solution was refluxed for 7 h and stirred for 12 h at room temperature. The reaction mixture was evaporated to dryness. The remaining solid residue was dissolved in 150 ml ethylacetate. The organic phase was washed with 5% aqueous citric acid and three times with water and dried over $MgSO_4$. Filtration and evaporation to dryness gave 3.8 g crude material. The crude N-(tert-butoxycarbonyl)-L-6-trifluoroacetamino-tryptophan HDP 30.2381 was purified by flash chromatography on a 330 g silica gel column (detection-wavelength 254 nm) with a gradient of $CHCl_3$+1% acetic acid to $CHCl_3$/MeOH (9:1)+1% acetic acid. After evaporation and co-evaporation with toluene HDP 30.2381 was isolated as a white solid (2.4 g, 41%).

¹H-NMR (400 MHz, $CDCl_3$, δ=ppm)

δ=1.41 [s, 9H, C(CH$_3$)$_3$]; 3.13-3.18 (m, 2H); 4.46-4.53 (m, 1H); 6.88 (s, 1H); 7.40-7.42 (m, 1H); 7.71 (s, 1H); 6.43-6.48 (m, 1H)

$^{13}$C-NMR (100 MHz, CDCl$_3$, δ=ppm)

δ=28.23, 31.10, 54.21, 69.49, 80.55, 104.39, 109.73, 113.31, 114.74, 118.96, 124.32, 125.84, 129.52, 135.72, 154.83, 155.66, 175.70

MS (ESI$^-$) found: 414.17 [M-H]$^-$; calc.: 414.13 (C$_{18}$H$_{19}$F$_3$N$_3$O$_5$)

MS (ESI$^-$) found: 829.17 [2M-H]$^-$; calc.: 829.26 (C$_{36}$H$_{39}$F$_6$N$_6$O$_{10}$)

MS (ESI$^-$) found: 1243.92 [3M-H]$^-$; calc.: 1243.39 (C$_{54}$H$_{58}$F$_9$N$_9$O$_{15}$)

4. Preparation of cis,trans-1-(tert-butoxycarbonyl)-2-carboxy-3α-hydroxy-6-trifluoroacetamino-1,2,3,3a,8,8a-hexahydropyrrolo[2,3-b]indole (cis-HDP 30.2416 and trans HDP 30.2416 (cis,trans-6-trifluoracetamino-Hpi))

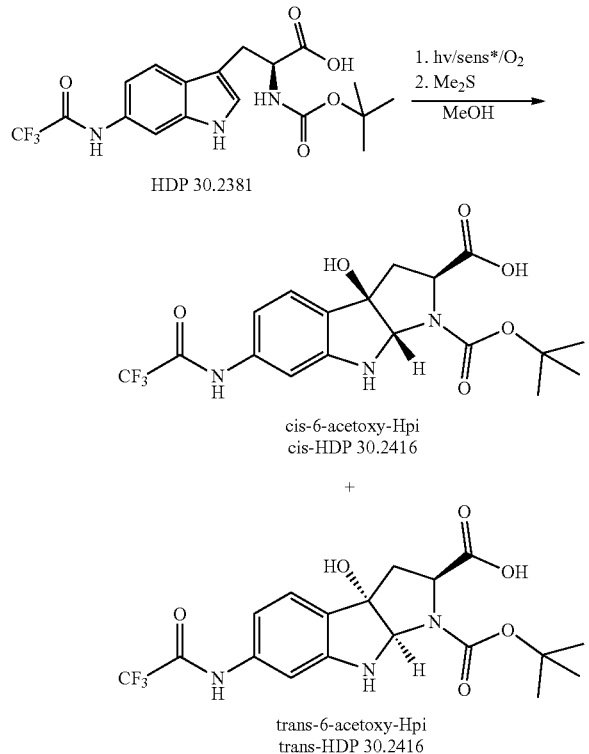

sens*: Rose Bengal

Photooxygenation

The photooxygenation was carried out with a 400 W high-pressure sodium vapor lamp (Sirius X400 lamp 230 V, 400 W; 55,000 lumen at a distance of 1.3 m) or alternatively with a tungsten-halogen lamp (500 W). A filter solution (CuCl$_2$—CaCO$_3$) cutting off light with λ<490 nm was used for a tungsten-halogen lamp.

Methylene blue or Rose Bengal was used as a dye sensitizer.

The reaction was carried out in a 500 ml cylindrical reaction vessel with heat exchange jacket made of DURAN® borosilicate glass, flat bottom and flat laboratory flange (DN) with two connectors with GL 18 thread. The distance from lamp to reaction vessel was 15 cm and the reaction temperature was in a range of 3-4° C.

Dry oxygen (99.5% purity) was bubbled through the reaction mixture with a rate of 2-4 l per minute.

The final product was purified on a Teledyne ISCO Flash chromatography system with a 330 g Silica Redi Sept Flash column (Teledyne ISCO cat. 69-2203-330). Solvents CH$_2$Cl$_2$, CH$_3$OH, CH$_3$COOH were standard HPLC or BP grade.

2.30 g (5.54 mmol) N-(tert-butoxycarbonyl)-6-trifluoracetylamino-L-tryptophan HDP 30.2381 and 160 mg Rose Bengal were dissolved in 500 ml methanol and cooled to 3° C. by using a Huber cryostat with glycol/water as cooling media. The reaction solution was irradiated with the 400 W high-pressure sodium vapor lamp. During the irradiation, a slow stream of oxygen was bubbled through the reaction solution. After 4 h irradiation, oxygenation and cooling were stopped and the reaction media was treated with 15 ml of dimethyl sulfide. The mixture was stirred for 2 h and evaporated to dryness by using a rotary evaporator with a water bath temperature of 35° C. The dark red residue was dried further in high vacuum to a crystalline solid (2.67 g). The crude product was purified on a 330 g silica gel column (detection wave length 254 nm) with a gradient of CH$_2$Cl$_2$+ 5% acetic acid to CH$_2$Cl$_2$/MeOH (15:1)+5% acetic acid. Yield 163 mg (8%) cis-HDP 30.2416 and 466 mg (20%) trans-HDP 30.2416 together with 297 mg cis/trans mixture. The product was co evaporated with toluene. After lyophilisation in tert-butanol both isomers were obtained as off-white powders.

cis-1-(tert-butoxycarbonyl)-2-carboxy-3α-hydroxy-6-trifluoroacetamino-1,2,3,3a,8,8a-hexahydropyrrolo[2,3-b]indole (cis-HDP 30.2416)

$^1$H-NMR (400 MHz, CD$_3$OD, δ=ppm)

δ=1.43, 1.54 (s, 9H, C(CH$_3$)$_3$); 2.45-2.63 (m, 2H, CH$_2$); 4.12-4.27 (m, 1H, 2-H); 5.35 (d, 1H, 8a-H); 6.92-7.12 (m, 2H, 7-H, 5-H); 7.20-7.25 (m, 1H, 4-H)

$^{13}$C-NMR (100 MHz, CD$_3$OD, δ=ppm)

δ=28.70, 31.11, 42.81, 61.73, 82.18, 85.11, 86.75, 104.20, 112.86, 124.64, 129.46, 139.21, 151.17, 156.06, 176.14

MS (ESI$^+$) found: 432.00 [M+H]$^+$; calc.: 432.14 (C$_{18}$H$_{21}$F$_3$N$_3$O$_6$)

MS (ESI$^+$) found: 454.17 [M+Na]$^+$; calc.: 454.13 (C$_{18}$H$_{20}$F$_3$N$_3$NaO$_6$)

MS (ESI$^+$) found: 862.92 [2M+H]$^+$; calc.: 863.26 (C$_{36}$H$_{41}$F$_6$N$_6$O$_{12}$)

MS (ESI$^+$) found: 885.08 [2M+Na]$^+$; calc.: 885.26 (C$_{36}$H$_{40}$F$_6$N$_6$NaO$_{12}$)

MS (ESI$^+$) found: 1315.67 [3M+Na]$^+$; calc.: 1316.39 (C$_{54}$H$_{60}$F$_9$N$_9$NaO$_{18}$)

UV/VIS (CH$_3$OH): λ$_{max}$=309 nm, 231 nm λ$_{min}$=285 nm trans-1-(tert-Butoxycarbonyl)-2-carboxy-3α-hydroxy-6-acetoxy-1,2,3,3a,8,8a-hexahydropyrrolo[2,3-b]indole (trans-HDP 30.2416)

$^1$H-NMR (400 MHz, CD$_3$OD, δ=ppm)

δ=1.44, 1.54 (s, 9H, C(CH$_3$)$_3$); 2.56-2.72 (m, 2H, CH$_2$); 4.50-4.56 (m, 1H, 2-H); 5.19-5.22 (d, 1H, 8a-H); 6.90-7.05 (m, 2H, 7-H, 5-H); 7.17-7.18 (m, 1H, 4-H)

$^{13}$C-NMR (100 MHz, CD$_3$OD, δ=ppm)

δ=28.05, 31.12, 40.40, 60.94, 69.45, 82.01, 84.87, 86.81, 103.65, 112.25, 124.95, 128.55, 139.46, 152.30, 156.05, 174.67

MS (ESI⁺) found: 432.08 [M+H]⁺; calc.: 432.14 ($C_{18}H_{21}F_3N_3O_6$)

MS (ESI⁺) found: 454.17 [M+Na]⁺; calc.: 454.13 ($C_{18}H_{20}F_3N_3NaO_6$)

MS (ESI⁺) found: 863.00 [2M+H]⁺; calc.: 863.26 ($C_{36}H_{41}F_6N_6O_{12}$)

MS (ESI⁺) found: 885.08 [2M+Na]⁺; calc.: 885.26 ($C_{36}H_{40}F_6N_6NaO_{12}$)

UV/VIS (CH₃OH): $\lambda_{max}$=312 nm, 233 nm
$\lambda_{min}$=286 nm

5. Solid Phase Synthesis of HDP 30.2528

Step 1: HDP 30.0013

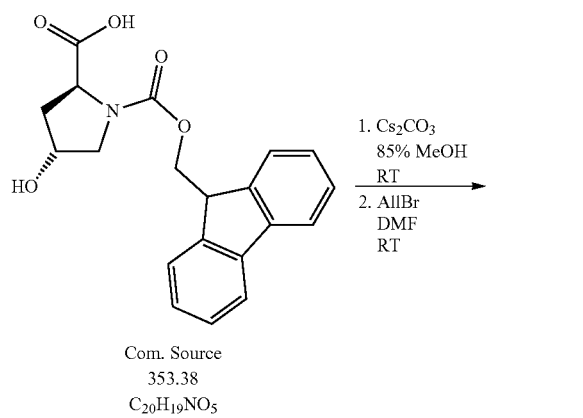

Com. Source
353.38
$C_{20}H_{19}NO_5$

HDP 30.0013
393.44
$C_{23}H_{23}NO_5$

FmocHypOH (10.0 g, 28.3 mmol) was suspended in 100 ml 80% MeOH and Cs₂CO₃ (4.6 g, 14.1 mmol) was added. The suspension was stirred at 50° C. for 30 minutes until complete dissolution. The reaction mixture was concentrated to dryness and redissolved in 100 ml DMF. Allylbromide (1.6 ml, 3.6 g, 29.7 mmol) was added dropwise and the reaction was stirred over night at room temperature. DMF was distilled off and the residue dissolved in tert-butylmethyl ether. Precipitates were filtered and the clear solution was absorbed on Celite prior column chromatography. The compound was purified on 220 g Silicagel with n-hexane/ethylacetate gradient. Yield: 11.5 g, 100%

Step 2: HDP 30.0400

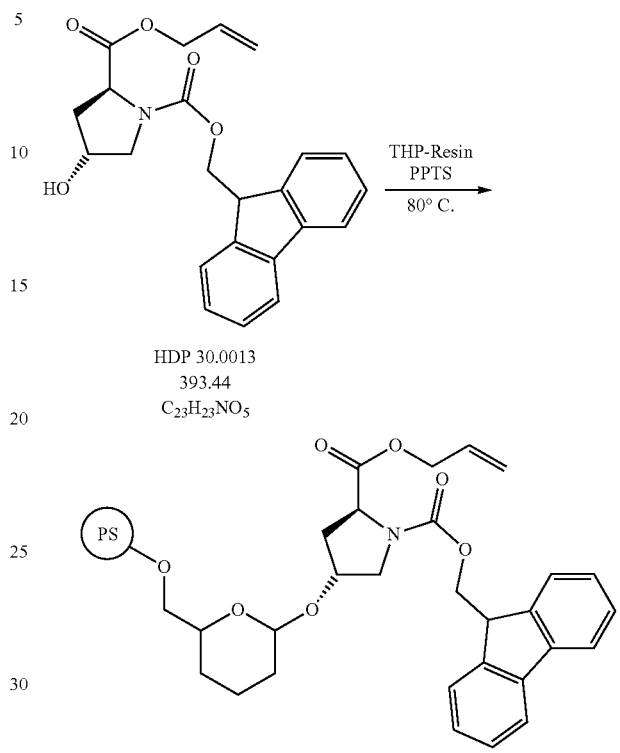

HDP 30.0013
393.44
$C_{23}H_{23}NO_5$

HDP 30.0400
393.44
$C_{23}H_{23}NO_5$

HDP 30.0013 (5.0 g, 14.1 mmol), Pyridinium 4-toluenesulfonate (1.33 g, 5.3 mmol) were added to a suspension of 1,3-dihydro-2H-pyran-2-yl-methoxymethyl resin (5.0 g, 1.0 mmol/g THP-resin) in 40 ml dichloroethane. The reaction was stirred at 80° C. overnight. After cooling the resin was filtered and extensively washed with dichloroethane, dimethylformamide, acetonitrile, dichloromethane and tert-butylmethylether.

Loading was 0.62 mmol/g (determined by UV-spectroscopy of the fluorenylmethyl group after deprotection)

Step 3: HDP 30.2516 (Solid Phase Synthesis)

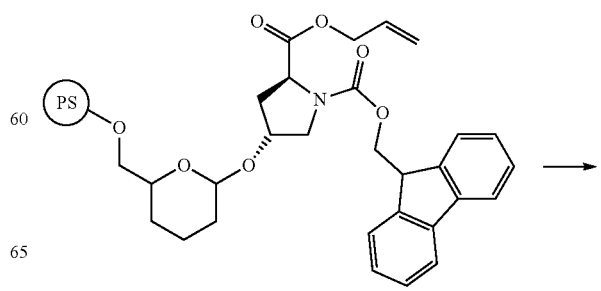

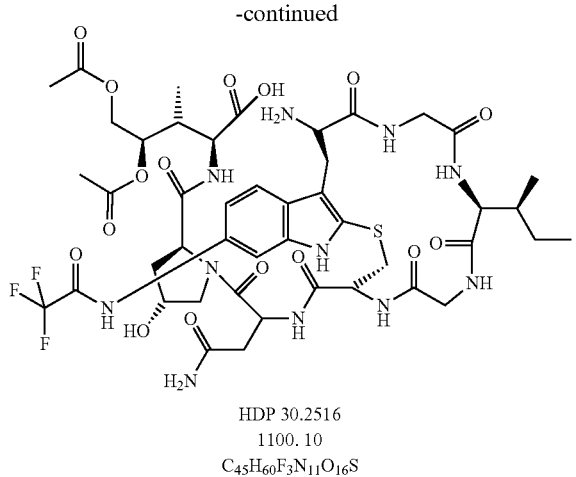

HDP 30.2516
1100. 10
$C_{45}H_{60}F_3N_{11}O_{16}S$

Resin Pre-Treatment:

HDP 30.0400 (0.31 g, 0.25 mmol) was treated with N,N-dimethylbarbituric acid (241 mg, 1.55 mmol) and Pd(PPh$_3$)$_4$ (35 mg, 0.03 mmol). The resin was shaken over night at room temperature. Thereafter the resin was extensively washed with dichloromethane, DMF, acetonitrile, dichloromethane and tert-butylmethyl ether and dried under reduced pressure.

Coupling Procedure:

All reactants and reagents were dissolved in Dichloromethane/DMF (1:1, v/v). HDP 30.0477 (described in EP 2872479B1) (102 mg, 0.30 mmol) was dissolved in 6.0 ml dichloromethane/N,N-dimethylformamide and treated with 4.0 ml of a 0.2 N solution PyBOP/HOBt and 2 ml DIEA (40% in DMF). After addition of 2.0 ml N,N-dimethylformamide, the reaction was heated to 50° C. for 8 minutes by microwave irradiation (20 W, CEM microwave reactor) and was washed with N,N-dimethylformamide after coupling.

Fmoc-Deprotection:

Deprotection was performed by addition of 6.0 ml 20% piperidine in N,N-dimethylformamide at 50° C. for 10 minutes. The resin was washed with N,N-dimethylformamide (no deprotection after coupling of the final amino acid).

All other amino acids were coupled following the above protocol, weightings are shown below:

| | | | |
|---|---|---|---|
| (0.102 g, 0.30 mmol) | 1.5 eq | HDP 30.0477 | MW: 39.6, see above) |
| 0.72 g, 1.2 mmol | 5.0 eq | FmocAsn(Trt)OH | MW: 599.7 |
| 0.71 g, 1.2 mmol | 5.0 eq | FmocCys(OTrt)OH | MW: 586.7 |
| 0.36 g, 1.2 mmol | 5.0 eq | FmocGlyOH | MW: 297.3 |
| 0.36 g, 1.2 mmol | 5.0 eq | FmocIleOH | MW: 353.4 |
| 0.36 g, 1.2 mmol | 5.0 eq | FmocGlyOH | MW: 297.3 |
| 0.161 g, 0.37 mmol | 1.5 eq | HDP 30.2416 | MW: 431.1 |

After completion, the resin was finally transferred into a syringe with bottom frit, washed with DCM and dried under reduced pressure.

Resin Release and B-Ring Formation

A solution of 5 ml TFA, 5 ml DCM plus 10% MeOH was aspirated to the resin and shaken for 15 min at ambient temperature. The solution was dispensed into a 50 ml reaction flask and the resin washed with TFA/DCM 1:1 plus 10% MeOH once and poured into the same flask. The reaction flask was stirred for 16 h. Triisopropylsilane (0.5 ml) was added and the reaction concentrated in vacuum. The residue was dissolved in 500 µl MeOH and the peptide precipitated in 50 ml ice-cold TBME. After centrifugation the supernatant was decanted and the precipitate washed once with 50 ml TBME and dried under reduced pressure.

The precipitate was solubilized in 2 ml methanol and purified by preparative reverse phase column chromatography. Methanol was distilled off under reduced pressure and the remaining aqueous phase was freeze dried.

Yield: 113 mg, 41%

MS (ESI$^+$) found: 1100.4 [M+H]$^+$; calc.: 1100.1 ($C_{45}H_{60}F_3N_{11}O_{16}S$)

HPLC: 99.1 area %

Step 4: Cyclisation (A-Ring Formation, HDP 30.2524)

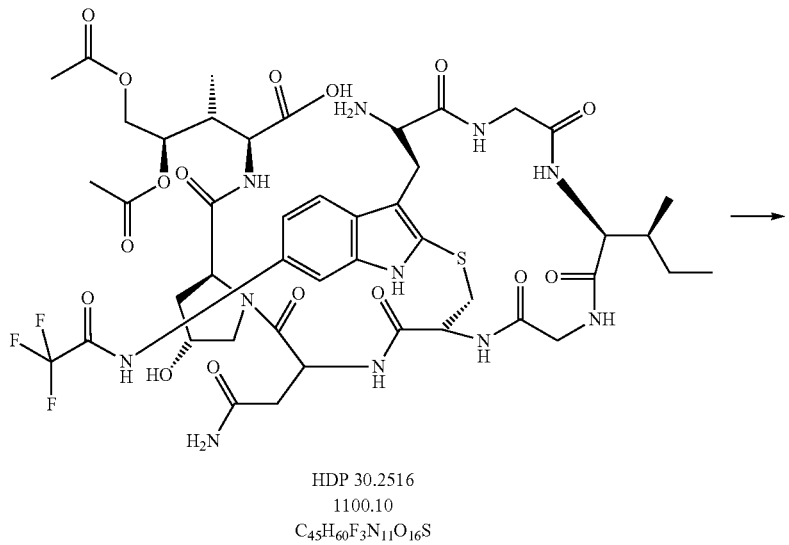

HDP 30.2516
1100.10
$C_{45}H_{60}F_3N_{11}O_{16}S$

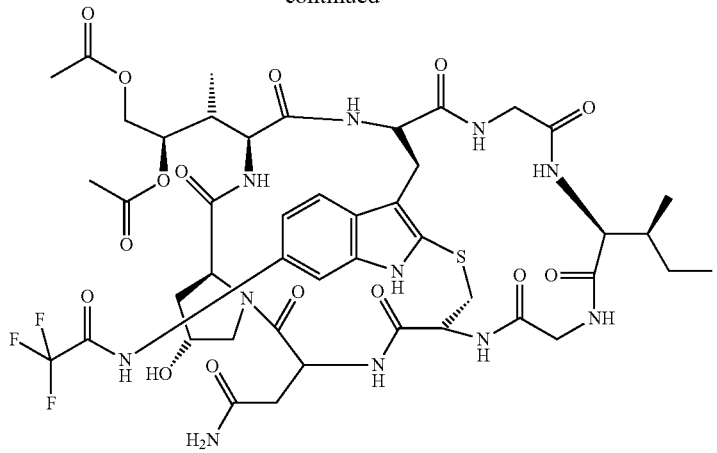

HDP 30.2524
1082.1
C₄₅H₅₈F₃N₁₁O₁₆S

The above freeze-dried monocyclic intermediate HDP 30.2516 (113 mg, 104 µmol) was dissolved in 5 ml DMF and treated with diphenylphosphorylazide (DPPA, 28 µl, 522 µmol, 5 eq) and Diisopropylethylamine (DIEA, 88 µl, 522 µmol, 5 eq). The reaction was stirred for 16 h and quenched with 500 µl water upon completion. Conversion was monitored by HPLC. The mixture was concentrated by reduced pressure, re-dissolved in 1 ml methanol and purified by preparative reverse phase column chromatography.

Yield: 43.6 mg, 38.6%

MS (ESI⁺) found: 1082.33 [M+H]⁺; calc.: 1082.1 ($C_{45}H_{58}F_3N_{11}O_{15}S$)

HPLC: 97.8 area %

Step 5: Acetate-Deprotection (HDP 30.2528)

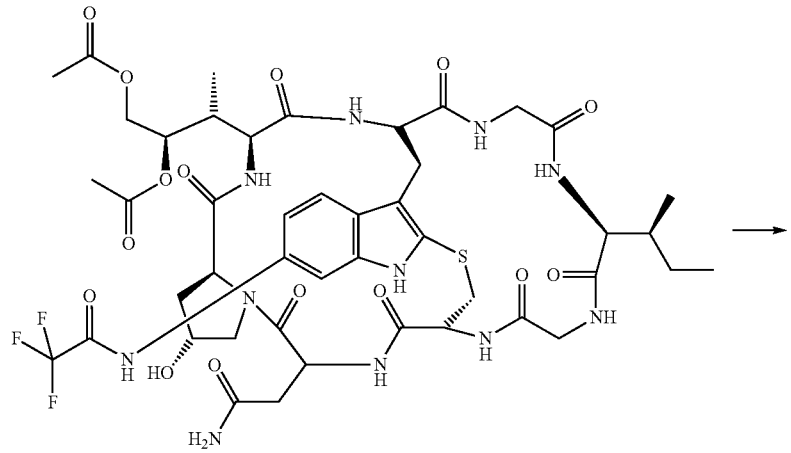

HDP 30.2524
1082.1
C₄₅H₅₈F₃N₁₁O₁₆S

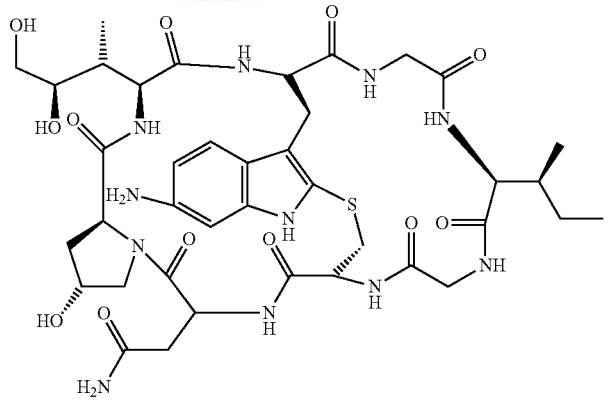

HDP 30.2528
902.0
$C_{39}H_{55}N_{11}O_{12}S$

HDP 30.2524 (33.6 mg, 31.1 μmol) was dissolved in a 7 N methanolic $NH_3$ solution (5.0 ml) and stirred. Conversion was checked by HPLC/MS. After completion (6-8 h) the reaction was concentrated in vacuum, re-suspended in 100 μl MeOH and purified by prep-HPLC.

Yield: 17.8 mg, 63.5%
HPLC: 100%
MS (ESI$^+$) found: 902.4 [M+H]$^+$; calc.: 902.00 ($C_{39}H_{55}N_{11}O_{12}S$)
found: 924.3 [M+Na]$^+$ 6. Preparation of 6-Maleimidopropionyl-L-Val-L-Al-PABA-S-deoxy-amanitin HDP 30.2560

6.1 Preparation of Maleimidopropionyl-L-Val-L-Ala-PABA HDP 30.2559

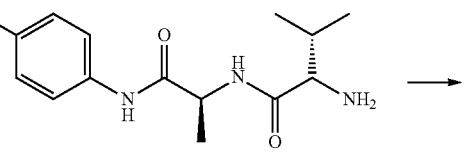

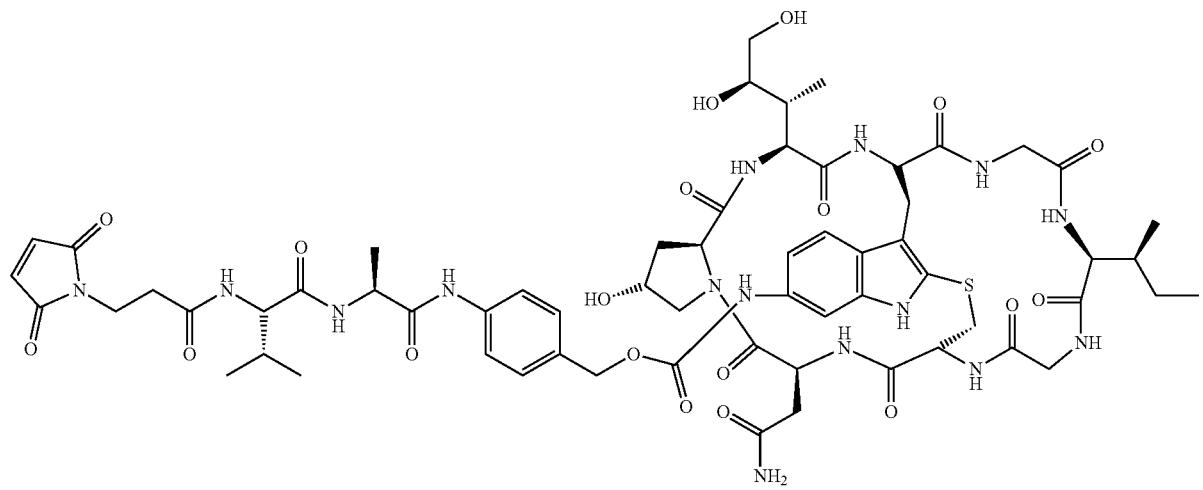

HDP 30.2560

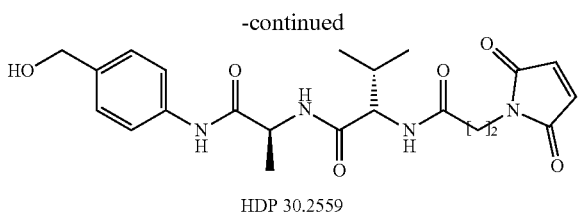

HDP 30.2559

5.87 g (10 mmol) NH$_2$-L-Val-L-Ala-PABA (prepared according to WO 2014/197871) was dissolved in 100 ml dry dimethylformamide (DMF). Under argon 2.66 g (10 mmol) 3-(maleimido)propionic acid-N-hydroxysuccinimide (BMPS) and 3.40 ml (20 mmol) diisopropylethylamine (DIPEA) were added at once. The reaction mixture was stirred at room temperature for 2 hours. The DMF was evaporated under vacuum and the residue treated with 150 ml methyl-tert-butylether. The organic solvent was discarded and the residue (4.57 g) purified on a 120 g silica gel column (detection wave length 246 nm) with a gradient of CH$_2$Cl$_2$ to CH$_2$Cl$_2$/MeOH (9:1). 1.98 g (44.6% yield) HDP 30.2559 were obtained as a brown solid.

MS (ESI$^+$) found: 445.17 [M+H]$^+$; calc.: 445.21 (C$_{22}$H$_{29}$N$_4$O$_6$)
MS (ESI$^+$) found: 467.25 [M+Na]$^+$; calc.: 467.19 (C$_{22}$H$_{28}$N$_4$NaO$_6$)
MS (ESI$^+$) found: 911.00 [2M+Na]$^+$; calc.: 911.39 (C$_{44}$H$_{56}$N$_8$NaO$_{12}$)
$^1$H NMR (500 MHz, DMSO-d$^6$)
δ=9.76 (s, 1H), 8.12 (d, J=7.1 Hz, 1H), 8.00 (d, J=8.3 Hz, 1H), 7.58-7.51 (m, 2H), 7.27-7.21 (m, 2H), 6.99 (s, 2H), 5.06 (bs, 1H), 4.43 (s, 2H), 4.39 (q, J=7.1 Hz, 1H), 4.13 (dd, J=8.3, 6.7 Hz, 1H), 3.69-3.55 (m, 2H), 2.49-2.40 (m, 2H), 2.03-1.89 (m, J=6.5 Hz, 1H), 1.31 (d, J=7.1 Hz, 3H), 0.86 (d, J=6.8 Hz, 3H), 0.83 (d, J=6.8 Hz, 3H).
$^{13}$C NMR (126 MHz, DMSO-d$^6$)
δ=170.78, 170.64, 170.62, 169.73, 137.47, 137.30, 134.44, 126.80, 118.78, 62.52, 57.71, 48.93, 33.96, 33.64, 30.18, 19.02, 18.07, 17.83, 0.01.

6.2 Preparation of Maleimidopropionyl-L-Val-L-Ala-PABA-4-nitrophenyl-carboxylate HDP 30.2586

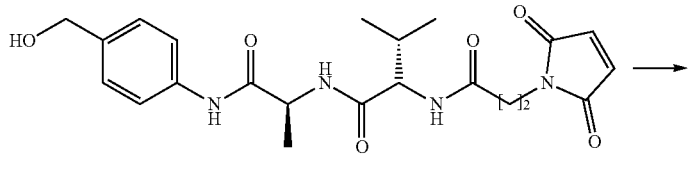

HDP 30.2559

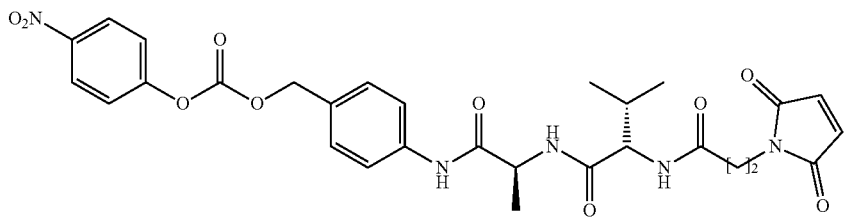

HDP 30.2586

200.0 mg (0.45 mmol) Maleimidopropionyl-L-Val-L-Ala-PABA HDP 30.2559 were dissolved in 4 ml dry dimethylformamide (DMF). 273.9 mg (0.90 mmol) bis-(4-nitrophenyl-carbonate) and 117.6 µl DIPEA (87.3 mg, 0.68 mmol) were added, and the reaction mixture was stirred for three hours at ambient temperature under argon. The reaction mixture was precipitated with 40 ml cold n-hexane/MTBE 1:1 and separated with a centrifuge. The solid was washed two times with cold MTBE and filtrated. The remaining solid is pure enough for the next step.

Yield 231.3 mg (84.3%) of a white solid
MS (ESI$^+$) found: 610.08 [M+H]$^+$; calc.: 609.21 (C$_{29}$H$_{31}$N$_5$O$_{10}$)
MS (ESI$^+$) found: 632.25 [M+Na]$^+$; calc.: 632.42 (C$_{29}$H$_{31}$N$_5$NaO$_{10}$)
MS (ESI$^+$) found: 1241.00 [2M+Na]$^+$; calc.: 1241.42 (C$_{58}$H$_{62}$N$_{10}$NaO$_{20}$)

6.3 Preparation of 6-Maleimidopropyonyl-L-Val-L-Al-PABA-S-deoxy-6-amino-amanitin HDP 30.2560

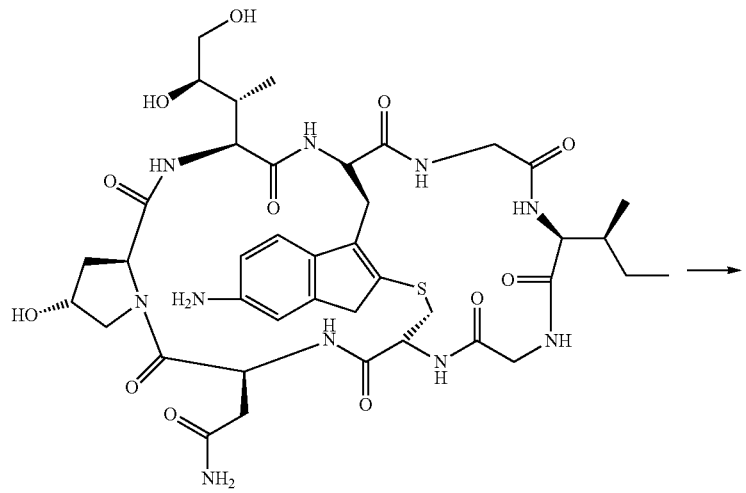

HDP 30.2528

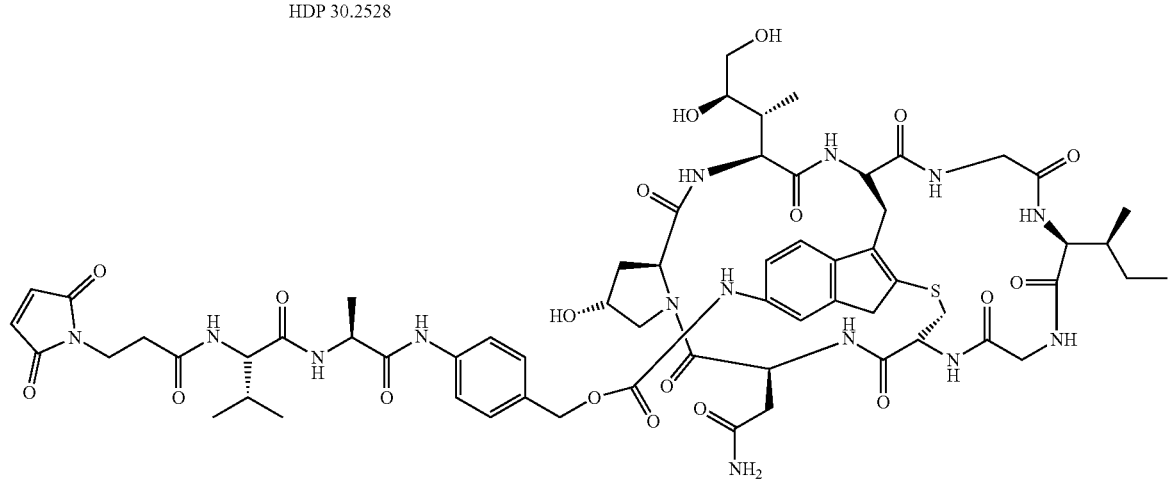

HDP 30.2560

6.73 mg (6.62 µmol) 6-amino-S-deoxy-amanitin HDP 30.2528 and 4.04 mg (6.62 µmol) maleimidopropionyl-L-Val-L-Ala-PABA-4-nitrophenyl-carboxylate HDP 30.2586 were dissolved in 100 µl dry dimethylformamide (DMF). 207 µl of the following solution, 9.02 mg (66.2 µmol) 1-hydroxy-7-azabenzotriazole (HOAt) in 2,070 µl dry dimethylformamide were added followed by 5.77 µl (33.6 µmol) diisopropylethylamine (DIPEA). The solution was stirred for 7 hours at room temperature under argon. The solvent was evaporated to dryness in high vacuum and the crude product purified by RP18 HPLC (Luna™ 10µ, 250×21 mm, Phenomenex®, 290 nm) with a gradient of 95% $H_2O$/5% MeOH to 95% MeOH/5%1-120 and a flow rate of 15 ml/min. The pure fraction was evaporated to dryness and freeze-dried in water yielding 3.71 mg (41%) HDP 30.2560 as an amorphous solid.

MS (ESI$^+$) found: 1394.50 [M+Na]$^+$; calc.: 1394.56 ($C_{62}H_{81}N_{15}NaO_{19}S$)

7. Preparation of 6-Maleimidohexenoyl-L-Val-L-Ala-PAB-S-deoxy-6-amino amanitin HDP 30.2540

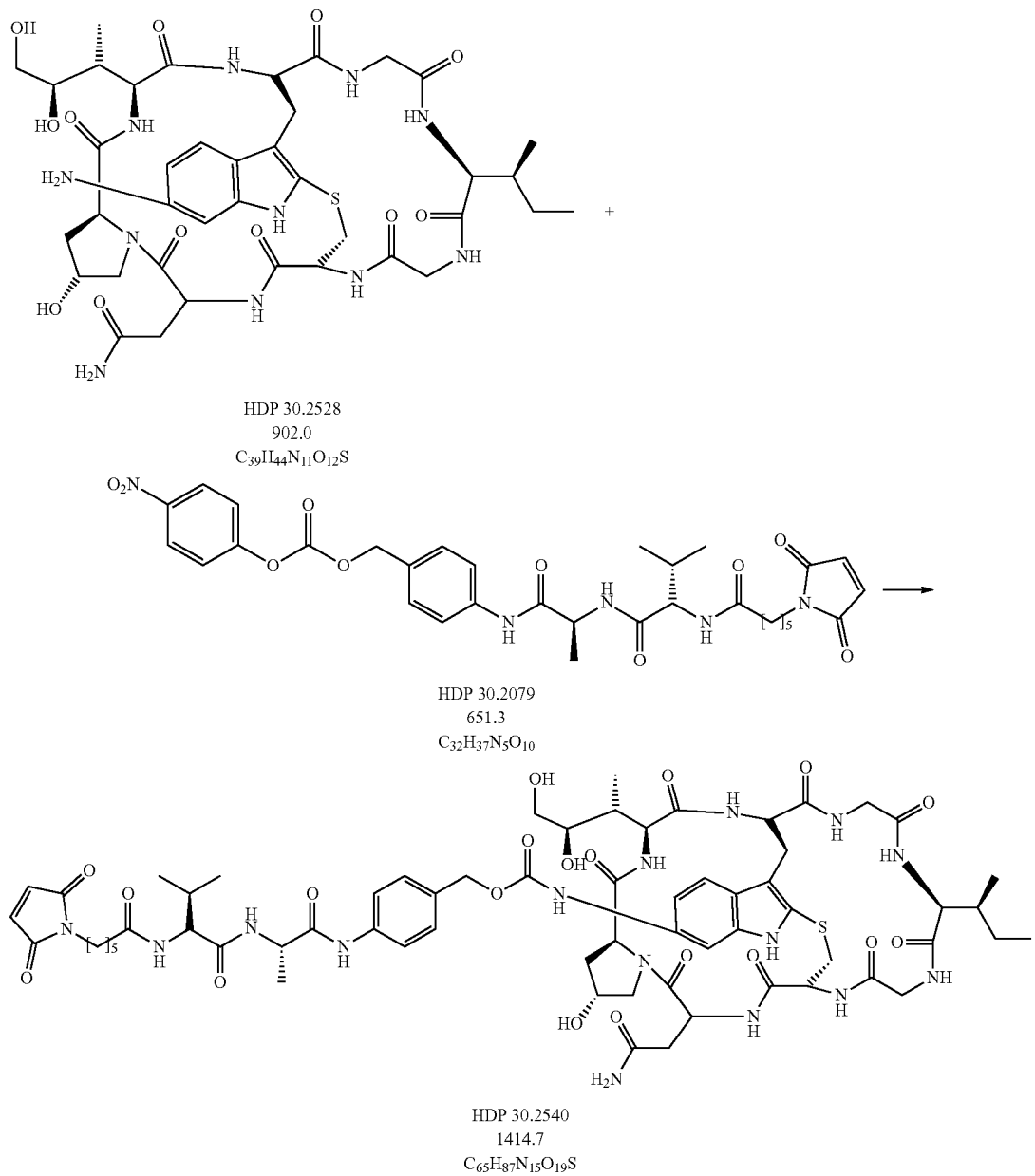

6-(Maleimido)hexanoyl-L-Val-L-Ala-PABA-4-nitrophenyl-carboxylate (HDP 30.2079) was prepared in analogy to step 6.1/6.2 with 6-(maleimido)hexanoic acid N-hydroxysuccinimide ester (EMCS) as starting material.

$^1$H NMR (500 MHz, DMSO-d$^6$) d 9.96 (s, 1H), 8.35-8.27 (m, 2H), 8.11 (d, J=7.0 Hz, 1H), 7.77 (d, J=8.6 Hz, 1H), 7.65 (d, J=8.5 Hz, 2H), 7.60-7.53 (m, 2H), 7.41 (d, J=8.6 Hz, 2H), 6.98 (s, 2H), 5.25 (s, 2H), 4.41 (p, J=7.1 Hz, 1H), 4.18 (dd, J=8.6, 6.8 Hz, 1H), 3.37 (t, J=7.1 Hz, 2H), 2.24-2.08 (m, 2H), 1.98 (h, J=6.8 Hz, 1H), 1.58-1.42 (m, 4H), 1.32 (d, J=7.0 Hz, 3H), 1.20 (p, J=7.6 Hz, 2H), 0.88 (d, J=6.7 Hz, 3H), 0.84 (d, J=6.8 Hz, 3H).

$^{13}$C NMR (126 MHz, DMSO-d$^6$) d 172.21, 171.10, 170.91, 170.89, 155.19, 151.82, 145.08, 139.32, 134.30, 129.28, 129.18, 125.25, 122.44, 118.98, 70.16, 57.50, 48.96, 36.92, 34.83, 30.23, 27.64, 25.69, 24.77, 19.09, 18.06, 17.78.

MS (ESI$^+$) found: 674.36 [M+Na]; calc.: 674.24 ($C_{32}H_{37}N_5NaO_{10}$)

HDP 30.2528 (5 mg, 5.5 μmol) was coupled with HDP 30.2079 (7.1 mg, 11.0 μmol) in 275 μl DMF and addition of diisopropylethylamine (9.4 μl, 55 μmol). After 16 h, HDP 30.2079 (3.5 mg, 5.4 μmol) and diisopropylethylamine (9.4 μl, 55 μmol) were added. The reaction was stirred for 4 days. The reaction mixture was directly purified by preparative chromatography.

Yield: 1.18 mg, 15.2%

HPLC: 100%

MS (ESI$^+$) found: 1437.6 [M+Na]$^+$; calc.: 1414.7 ($C_{65}H_{87}N_{15}O_{19}S$)

8. Synthesis of HDP 30.2540 and 30.2560 Conjugates

Example: Synthesis of T-D265C-30.2560

10 mg Thiomab T-D265C in PBS buffer were used for conjugation to HDP 30.2560.

Adjust antibody solution to 1 mM EDTA:
  2 ml antibody solution (10.0 mg)+20 µl 100 mM EDTA, pH 8.0
Amount antibody: 10 mg=$6.9 \times 10^{-8}$ mol
Uncapping of cysteines by reaction of antibody with 40 eq. TCEP:
  2 ml antibody solution ($6.9 \times 10^{-8}$ mol)+55.2 µl 50 mM TCEP solution ($2.76 \times 10^{-6}$ mol)
  Incubate for 3 h at 37° C. on a shaker.
  Two consecutive dialyses at 4° C. in 2.0 l 1×PBS, 1 mM EDTA, pH 7.4 in a Slide-A-Lyzer Dialysis Cassette 20,000 MWCO, first dialysis ca. 4 h, second dialysis overnight
Oxidation by reaction of antibody with 20 eq. dehydroascorbic acid (dhAA):
  ca. 2 ml antibody solution ($6.9 \times 10^{-8}$ mol)+27.6 µl fresh 50 mM dhAA solution ($1.38 \times 10^{-6}$ mol)
  Incubate for 3 h at RT on a shaker.
Conjugation with amanitin using 6 eq. HDP 30.2560 and quenching with 25 eq. N-acetyl-L-cysteine:
  Solubilize 2 mg HDP 30.2560 in 200 µl DMSO=10 µg/µl
  ca. 2 ml antibody solution (=9.5 mg; $6.53 \times 10^{-8}$ mol)+53.8 µl HDP 30.2560 (=538 µg; $3.92 \times 10^{-7}$ mol).
  Incubate 1 h at RT.
  Quench by addition of 16.3 µl 100 mM N-acetyl-L-cysteine ($1.63 \times 10^{-6}$ mol).
  Incubate 15 min at RT (or overnight at 4° C.).
  Purify reaction mix with 1×PD-10 column equilibrated with 1×PBS, pH 7.4. Identify protein-containing fractions with Bradford reagent on parafilm and bring protein-containing fractions together.
  Dialysis of antibody solution at 4° C. overnight in 2.0 l PBS, pH 7.4 and Slide-A-Lyzer Dialysis Cassettes 20,000 MWCO.
  Determination of Drug-Antibody-Ratio (DAR) by LC-ESI-MS-Analysis.
  Adjust protein concentration to 5.0 mg/ml ($3.4 \times 10^{-5}$ M) and bring to sterile conditions by filtration. Store at 4° C.

ADCs with a different antibody or with HDP 30.2540 were produced accordingly. The molecular amount of antibody was calculated according to the MW of the respective antibody. The amounts of linker toxin, TCEP, dhAA, N-acetyl-L-cysteine were adjusted accordingly to reach the respective equivalents.

9. In Vitro Cytotox of 6'-Amino-Amaninamide 30.2528

BrdU Cell Proliferation Assay on HEK293 and HEK293 OATP1B3 cells
HEK293-OATP1B3 cell culture plates were coated with poly-D-lysine.
  Coating with Poly-D-Lysine:
  5 mg poly D-lysine in 50 ml sterile water
  50 µl in each well of a 96 well plate
  Incubation for 1 h at RT
  Washing of wells twice with 200 µl sterile water
  Drying for at least for 2 h (RT)
Black 96-well plates with clear bottom with $2.0 \times 10^3$ HEK293 and HEK293 OATP1B3 cells/well and 90 µl growth medium per well including 10% FCS and supplements were prepared. Controls: "Blank" was set up with 100 µl medium without cells, "Background" and "100%" were set up with cells in 100 µl medium.
Incubation for 24 h at 37° C. and 5% $CO_2$.
Dilution Scheme of HDP 30.2528 and Alpha-Amanitin:
The stock solutions were diluted 1:1,000 (1:10 and 1:100 dilution) in medium:
  10 µl Amanitin derivative stock solution ($1.0 \times 10^{-2}$ M)+90 µl PBS=100 µl $1.0 \times 10^{-3}$ M
  2 µl dilution+198 µl medium=200 µl $1 \times 10^{-5}$ M
Further Dilutions:
  A: 200 µl $1.0 \times 10^{-5}$ M
  B: 80 µl growth medium+20 µl solution A (1:5 dilution)
  C: 80 µl growth medium+20 µl solution B (1:5 dilution)
  D: 80 µl growth medium+20 µl solution C (1:5 dilution)
  E: 80 µl growth medium+20 µl solution D (1:5 dilution)
  F: 80 µl growth medium+20 µl solution E (1:5 dilution)
  G: 80 µl growth medium+20 µl solution F (1:5 dilution)
  H: 80 µl growth medium+20 µl solution G (1:5 dilution)
  10 µl of each solution were added to well triplicates. Final volume: 100 µl/well.
Final dose: starting $1 \times 10^{-6}$ M; 1:5 dilution series.
Incubation for 96 h at 37° C. and 5% $CO_2$.
After 96 h: Roche Cell proliferation assay, luminescent according to manufacturer instructions.
$EC_{50}$-concentrations were determined with Graphpad Prism 4.0 data analysis software.

10.: In Vitro Cytotox of HDP 30.2560 and HDP 30.2540 Conjugates

BrdU Cell Proliferation Assay on SKBR-3, JIMT-1, LnCap, and 22rv1 Cells
The assay was performed as described above (9.) with the following changes:
Cell culture plates were not coated with poly-D-lysine.
Dilution scheme of ADCs:
The stock solutions were diluted to $1.0 \times 10^{-6}$ M in growth medium
Further dilutions:
  A: 100 µl $1.0 \times 10^{-6}$ M
  B: 80 µl growth medium+20 µl solution A (1:5 dilution)
  C: 80 µl growth medium+20 µl solution B (1:5 dilution)
  D: 80 µl growth medium+20 µl solution C (1:5 dilution)
  E: 80 µl growth medium+20 µl solution D (1:5 dilution)
  F: 80 µl growth medium+20 µl solution E (1:5 dilution)
  G: 80 µl growth medium+20 µl solution F (1:5 dilution)
  H: 80 µl growth medium+20 µl solution G (1:5 dilution)
  10 µl of each solution were added to well triplicates. Final volume: 100 µl/well.
Final dose: starting $1 \times 10^{-7}$ M; 1:5 dilution series
WST-1 Assay on Raji Cells and Nalm-6 Cells:
Transparent F-bottom 96-well plates with $2.0 \times 10^3$ cells/well and 90 µl of the respective growth medium per well including 10% FCS and supplements were prepared. Controls: "Blank" was set up with 100 µl medium without cells; "cells only" was set up with cells in 100 µl medium.
Incubation for 24 h at 37° C. and 5% $CO_2$.
Dilution scheme of ADCs:
The stock solutions were diluted to $1.0 \times 10^{-6}$ M in growth medium
Further Dilutions:
  A: 100 µl $1.0 \times 10^{-6}$ M
  B: 80 µl growth medium+20 µl solution A (1:5 dilution)
  C: 80 µl growth medium+20 µl solution B (1:5 dilution)

D: 80 µl growth medium+20 µl solution C (1:5 dilution)
E: 80 µl growth medium+20 µl solution D (1:5 dilution)
F: 80 µl growth medium+20 µl solution E (1:5 dilution)
G: 80 µl growth medium+20 µl solution F (1:5 dilution)
H: 80 µl growth medium+20 µl solution G (1:5 dilution)
10 µl of each solution were added to well triplicates. Final volume: 100 µl/well.

Final dose: starting $1\times10^{-7}$M; 1:5 dilution series

Incubation for 96 h at 37° C. and 5% $CO_2$.

After 96 h: Roche WST-1 Cell Proliferation assay according to manufacturer instructions.

$EC_{50}$-concentrations were determined with Graphpad Prism 4.0 data analysis software.

The invention claimed is:

1. A method of treating cancer in a patient, the method comprising administering to the patient a conjugate comprising:
   (a) an amanitin derivative comprising a 6'-amino-substituted tryptophan moiety, which is selected from (i)S-desoxy-6'-amino-amanin, 6'-amino-amanin, (ii)S-desoxy-6'-amino-amanin-amide, 6'-amino-amaninamide, and (iii) a derivative of the amanitin derivative according to (i), wherein the free carboxylic acid moiety of amino acid 1 is converted to an carboxylic ester —C(=O)OR4 or to a moiety —C(=O)NH—OR4,
   (b) a target-binding moiety, and
   (c) optionally a linker linking said amanitin derivative and said target-binding moiety, wherein the cancer is selected from the group consisting of breast cancer, pancreatic cancer, cholangiocarcinoma, colorectal cancer, prostate cancer, leukemia, and malignant lymphoma, and
   wherein the cancer is responsive to inhibition of mammalian RNA polymerase II.

2. A method of treating cancer in a patient, the method comprising administering to the patient a pharmaceutical composition comprising a conjugate comprising:
   (a) an amanitin derivative comprising a 6'-amino-substituted tryptophan moiety, which is selected from (i)S-desoxy-6'-amino-amanin, 6'-amino-amanin, (ii)S-desoxy-6'-amino-amanin-amide, 6'-amino-amaninamide, and (iii) a derivative of the amanitin derivative according to (i), wherein the free carboxylic acid moiety of amino acid 1 is converted to an carboxylic ester —C(=O)OR4 or to a moiety —C(=O)NH—OR4,
   (b) a target-binding moiety, and
   (c) optionally a linker linking said amanitin derivative and said target-binding moiety,
   wherein the cancer is selected from the group consisting of breast cancer, pancreatic cancer, cholangiocarcinoma, colorectal cancer, prostate cancer, leukemia, and malignant lymphoma, and
   wherein the cancer is responsive to inhibition of mammalian RNA polymerase II.

3. The method of treating cancer in a patient of claim 1, wherein the amanitin derivative is selected from S-desoxy-6'-amino-amanin, 6'-amino-amanin, S-desoxy-6'-amino-amaninamide, and 6'-amino-amaninamide.

4. The method of treating cancer in a patient of claim 2, wherein the amanitin derivative is selected from S-desoxy-6'-amino-amanin, 6'-amino-amanin, S-desoxy-6'-amino-amaninamide, and 6'-amino-amaninamide.

* * * * *